United States Patent
Shibata et al.

(10) Patent No.: US 10,299,672 B2
(45) Date of Patent: May 28, 2019

(54) SUBJECTIVE OPTOMETRIC APPARATUS

(71) Applicant: NIDEK CO., LTD., Gamagori, Aichi (JP)

(72) Inventors: Kazunori Shibata, Aichi (JP); Ryoji Suzuki, Aichi (JP); Yukito Hirayama, Aichi (JP); Hidenori Kanda, Aichi (JP)

(73) Assignee: NIDEK CO., LTD., Gamagori, Aichi (JP)

( * ) Notice: Subject to any disclaimer, the term of this patent is extended or adjusted under 35 U.S.C. 154(b) by 0 days.

(21) Appl. No.: 15/827,023

(22) Filed: Nov. 30, 2017

(65) Prior Publication Data

US 2018/0153392 A1 Jun. 7, 2018

(30) Foreign Application Priority Data

Dec. 1, 2016 (JP) .................................. 2016-234521

(51) Int. Cl.
*A61B 3/02* (2006.01)
*A61B 3/14* (2006.01)
(Continued)

(52) U.S. Cl.
CPC .......... *A61B 3/0091* (2013.01); *A61B 3/0008* (2013.01); *A61B 3/0075* (2013.01);
(Continued)

(58) Field of Classification Search
CPC ........... A61B 3/032; A61B 3/04; A61B 3/036; A61B 3/066; A61B 3/02; A61B 3/18;
(Continued)

(56) References Cited

U.S. PATENT DOCUMENTS

| | | | | |
|---|---|---|---|---|
| 6,244,713 B1 * | 6/2001 | Hayashi | ................. | A61B 3/032 351/243 |
| 2001/0028440 A1 * | 10/2001 | Iwanaga | ................. | A61B 3/152 351/208 |
| 2014/0185012 A1 * | 7/2014 | Kanazawa | ............. | A61B 3/032 351/237 |

FOREIGN PATENT DOCUMENTS

| | | | |
|---|---|---|---|
| EP | 1 042 984 A1 | 10/2000 | |
| EP | 1 442 696 A1 | 8/2004 | |

(Continued)

OTHER PUBLICATIONS

Communication dated Apr. 6, 2018, issued by the European Patent Office in counterpart European application No. 17204901.7.

*Primary Examiner* — Dawayne Pinkney
(74) *Attorney, Agent, or Firm* — Sughrue Mion, PLLC

(57) ABSTRACT

A subjective optometric apparatus includes: a projection optical system that includes a target presenting unit configured to emit a target light flux, the projection optical system being configured to project, onto an examinee's eye, the target light flux emitted from the target presenting unit; a housing configured to accommodate the projection optical system; a presentation window configured to project the target light flux onto the examinee's eye by transmitting the target light flux emitted from the projection optical system and outputting the target light flux from an inside of the housing to an outside of the housing; and an observation unit configured to observe, via the presentation window, a positional relationship between the examinee's eye and an eye refractivity measuring unit configured to change an optical property of the target light flux output from the inside of the housing to the outside of the housing.

16 Claims, 13 Drawing Sheets

(51) Int. Cl.
*A61B 3/10* (2006.01)
*A61B 3/00* (2006.01)
*A61B 3/028* (2006.01)
*A61B 3/032* (2006.01)
*A61B 3/15* (2006.01)

(52) U.S. Cl.
CPC ............ *A61B 3/028* (2013.01); *A61B 3/0285* (2013.01); *A61B 3/032* (2013.01); *A61B 3/14* (2013.01); *A61B 3/152* (2013.01)

(58) Field of Classification Search
CPC ......... A61B 3/1015; A61B 3/103; A61B 3/08; A61B 3/14; A61B 3/152; A61B 3/113; A61B 3/1225; A61B 3/024; G09B 17/04; G02C 5/00
USPC ......... 351/237, 233, 238, 240–246, 41, 200, 351/201, 205–206, 208–211, 216, 351/221–223
See application file for complete search history.

(56) References Cited

FOREIGN PATENT DOCUMENTS

| | | |
|---|---|---|
| EP | 2 949 266 A1 | 12/2015 |
| JP | 5-176893 A | 7/1993 |
| JP | 2014-57686 A | 4/2014 |
| WO | 2008/083015 A2 | 7/2008 |

\* cited by examiner

SUBJECTIVE OPTOMETRIC APPARATUS

BACKGROUND

This disclosure relates to a subjective optometric apparatus for subjectively measuring optical properties of an examinee's eye.

There is known a subjective optometric apparatus that examines (measures) refractivity and the like of an examinee's eye by using an eye refractivity measuring unit that is disposed in front of the examinee's eye, in which an optical element such as a spherical lens or a cylinder (astigmatic) lens is disposed in a test window of the eye refractivity measuring unit, and a target is presented to the examinee's eye through the disposed optical element (see JP-A-5-176893). At this time, the examinee looks into the test window of the eye refractivity measuring unit, thereby checking the visual appearance of the presented target.

SUMMARY

Incidentally, in a case of using an eye refractivity measuring unit in a subjective optometric apparatus, position adjustment between the eye refractivity measuring unit and an examinee's eye is performed such that the examinee checks a target through a test window. In the related art, when the position adjustment between the eye refractivity measuring unit and the examinee's eye is performed, a positional relationship between the examinee's eye and the eye refractivity measuring unit is observed from a side opposite to a side on which the examinee looks into the test window of the eye refractivity measuring unit, and then the position adjustment is performed. At this time, an examiner makes an observation by putting his or her head between the eye refractivity measuring unit and a housing that accommodates a projection optical system which projects a target light flux onto the examinee's eye. Therefore, the examiner needs to perform the position adjustment between the examinee's eye and the eye refractivity measuring unit while the examiner is in an unnatural posture, and thus a burden is imposed on the examiner. In addition, it is difficult to observe a relationship between the eye refractivity measuring unit and the examinee's eye in some cases, or it is not possible to perform the position adjustment with high accuracy.

This disclosure is made in consideration of the problem in the related art, and a technical object thereof is to provide a subjective optometric apparatus that is capable of easily performing position adjustment between an examinee's eye and an eye refractivity measuring unit.

In order to achieve the object described above, this disclosure includes the following configurations.

A subjective optometric apparatus comprising:

a projection optical system that includes a target presenting unit configured to emit a target light flux, the projection optical system being configured to project, onto an examinee's eye, the target light flux emitted from the target presenting unit;

a housing configured to accommodate the projection optical system;

a presentation window configured to project the target light flux onto the examinee's eye by transmitting the target light flux emitted from the projection optical system and outputting the target light flux from an inside of the housing to an outside of the housing; and an observation unit configured to observe, via the presentation window, a positional relationship between the examinee's eye and an eye refractivity measuring unit configured to change an optical property of the target light flux output from the inside of the housing to the outside of the housing.

A subjective optometric apparatus comprising:

a projection optical system that has a target presenting unit configured to emit a target light flux and configured to project, onto an examinee's eye, the target light flux emitted from the target presenting unit;

a housing that accommodates the projection optical system;

a presentation window configured to project the target light flux onto the examinee's eye by transmitting the target light flux emitted from the projection optical system and outputting the target light flux from an inside of the housing to an outside of the housing;

an eye refractivity measuring unit that includes a pair of right and left lens chamber units that dispose optical elements in a test window in a switchable manner;

a cornea position alignment optical system that is disposed in the eye refractivity measuring unit and is used to check an inter-vertex distance between a lens wearing reference position and a cornea vertex of the examinee's eye;

a checking window for checking the cornea position alignment optical system disposed from the outside of the eye refractivity measuring unit; and a light guiding unit configured to observe the checking window.

DESCRIPTION OF ILLUSTRATIVE EMBODIMENTS

<Overview>

Figure 1:
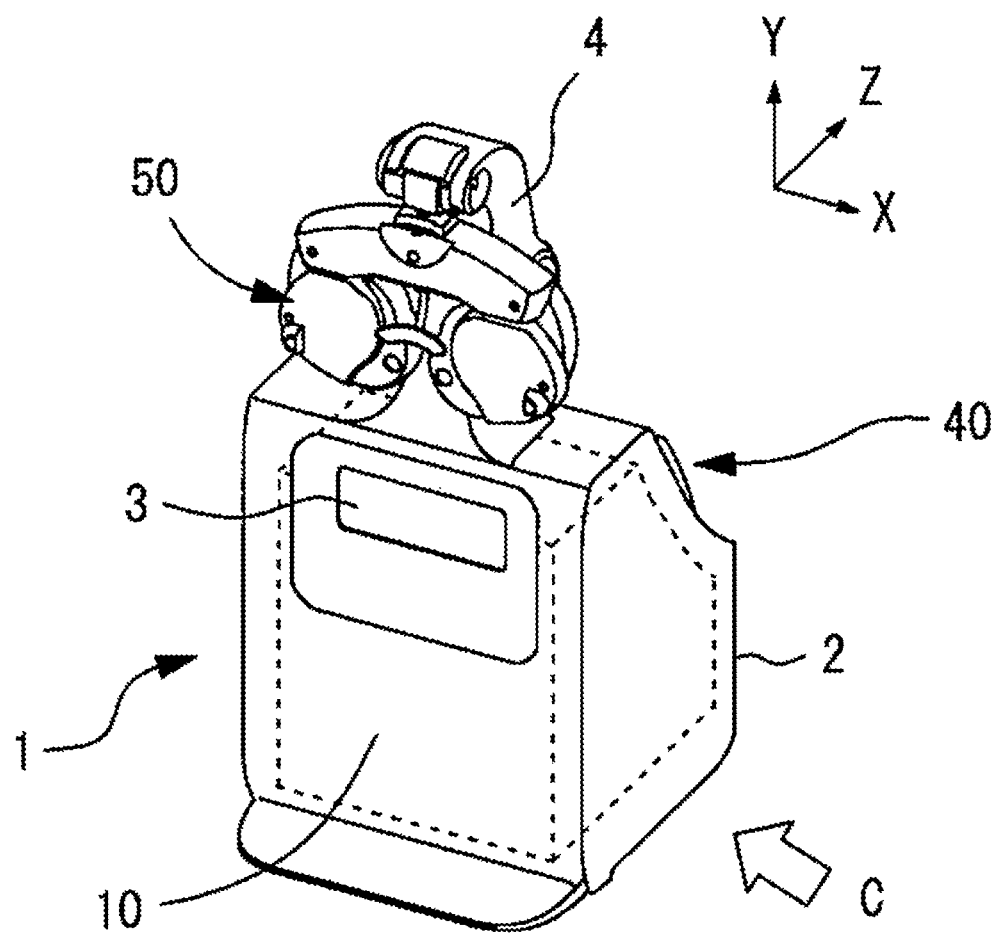
FIG. 1 is a perspective view illustrating a subjective optometric apparatus viewed from a front side.

Hereinafter, a typical embodiment will be described with reference to the accompanying figures. FIGS. 1 to 16 are diagrams for describing an optometric apparatus and an optometric program according to the embodiment. The following items classified by < > are used individually or in association with each other.

In the following description, a depth direction (frontward-rearward direction of an examinee during measurement of the examinee) of a subjective optometric apparatus is referred to as a Z direction, a horizontal direction (rightward-leftward direction of the examinee during the measurement of the examinee) on a plane perpendicular to the depth direction is referred to as an X direction, and a vertical direction (upward-downward direction of the examinee during the measurement of the examinee) is referred to as a Y direction.

For example, the subjective optometric apparatus (for example, a subjective optometric apparatus 1) in the embodiment includes a projection optical system (for example, a projection optical system 10). For example, the projection optical system has a target presenting unit (for example, a display 11). For example, the target presenting unit emits a target light flux.

For example, the subjective optometric apparatus includes a housing (for example, a housing 2) that accommodates the projection optical system. For example, the housing accommodates the projection optical system.

For example, the subjective optometric apparatus includes a presentation window (for example, a presentation window 3). For example, the presentation window may be used to project the target light flux onto the examinee's eye by transmitting the target light flux emitted from the projection optical system and outputting the target light flux from the inside of the housing to the outside of the housing.

For example, the projection optical system projects, onto an examinee's eye, the target light flux emitted from the target presenting unit. For example, the projection optical system may include at least one optical member that projects the target light flux onto the examinee's eye.

For example, a configuration in which the display is used as the target presenting unit may be employed. For example, a liquid crystal display (LCD), an organic electroluminescence (EL), or the like is used as the display. For example, an examination target or the like such as a Landolt ring target is displayed on the display.

For example, a digital micromirror device (DMD) may be used as the target presenting unit. In general, DMD has a high reflectance and is bright. Therefore, it is possible to maintain the intensity of the target light flux, compared to a case of using a liquid crystal display using polarized light.

For example, the target presenting unit may be configured to include a visible light source for presenting the target and a target plate. In this case, for example, the target plate is a rotatable disc plate and is provided with a plurality of targets. For example, the plurality of targets include a target for a vision examination or the like which is used during subjective measurement. For example, as the target for the vision examination, a target (a visual acuity value of 0.1, 0.3, . . . , or 1.5) for each visual acuity value is prepared. For example, the target plate rotates by a motor or the like, and the targets are disposed in a switchable manner on an optical path through which the target light flux is guided to the examinee's eye. It is needless to say that another target presenting unit having another configuration may be used as the target presenting unit that projects the target light flux.

For example, in the embodiment, the projection optical system may include a right-eye projection optical system and a left-eye projection optical system provided as a pair on the right and left sides. In this case, for example, the target presenting units may be provided as a pair on the right and left sides. For example, the right-eye projection optical system and the left-eye projection optical system may have a configuration in which the right-eye projection optical system is configured to include the same members as those the left-eye projection optical system. In addition, for example, the right-eye projection optical system and the left-eye projection optical system may have a configuration in which at least some members that configure the right-eye projection optical system are different from members that configure the left-eye projection optical system. For example, the right-eye projection optical system and the left-eye projection optical system may have a configuration in which at least some members that configure the right-eye projection optical system serve as members that configure the left-eye projection optical system. In addition, for example, the right-eye projection optical system and the left-eye projection optical system may have a configuration in which members that configure the right-eye projection optical system are separately provided from members that configure the left-eye projection optical system.

For example, the subjective optometric apparatus may include an eye refractivity measuring unit (for example, an eye refractivity measuring unit 50). In this case, for example, the target light flux is projected onto the examinee's eye via the eye refractivity measuring unit. For example, the eye refractivity measuring unit may be configured to change an optical property of the target light flux (for example, at least one of a spherical diopter power, a cylindrical power, a cylindrical axis, a polarization property, and an aberration amount). For example, a configuration of controlling an optical element may be employed as a configuration of changing the optical property of the target light flux. For example, a configuration of using a wavefront modulation element may be employed. For example, the eye refractivity measuring unit may be configured to include a pair of right and left lens chamber units that dispose optical elements in a test window in a switchable manner. For example, the subjective optometric apparatus includes the eye refractivity measuring unit that changes the optical property of the target light flux output from the inside of the housing to the outside of the housing. In this manner, an examiner can easily perform the subjective examination on the examinee's eye.

For example, the subjective optometric apparatus may have a configuration in which the housing and the eye refractivity measuring unit are disposed to be close to each other. For example, in the configuration of close disposition, there is a distance between the eye refractivity measuring unit 50 and the housing 2 to the extent that the examiner's head cannot be put therebetween. For example, in the configuration of close disposition, the distance between the eye refractivity measuring unit 50 and the housing 2 may be 1 m or shorter (for example, 1 m, 500 mm, 135 mm, or 70 mm). It is needless to say that, in the configuration of close disposition, the distance between the eye refractivity measuring unit 50 and the housing 2 may be 1 m or shorter.

<Checking of Positional Relationship Between Eye Refractivity Measuring Unit and Examinee's Eye>

For example, the subjective optometric apparatus may include an observation unit (for example, an observation unit 40). For example, the observation unit may be used to observe, via the presentation window, a positional relationship between the examinee's eye and the eye refractivity measuring unit (for example, the eye refractivity measuring unit 50) that changes the optical property of the target light flux outputting from the inside of the housing to the outside of the housing. For example, the subjective optometric apparatus includes the observation unit for observing, via the presentation window, the positional relationship between the examinee's eye and the eye refractivity measuring unit that changes the optical property of the target light flux output from the inside of the housing to the outside of the housing. In this manner, the examiner can easily check the positional relationship between the eye refractivity measuring unit and the examinee's eye and can easily perform position adjustment between the examinee's eye and the eye refractivity measuring unit.

For example, the observation unit may be disposed outside of an optical path through which the target light flux passes. In this case, for example, in a configuration in which the observation unit is disposed outside of the optical path, the observation unit may be disposed in any one direction of the rightward, leftward, upward, and downward directions with respect to the optical path through which the target light flux passes such that the target light flux is outside of the optical path. When the observation unit is disposed outside of the optical path, a configuration in which at least a part of the observation unit is outside of the optical path may be employed, and the observation unit does not need to be completely outside of the optical path. In this case, for example, in a configuration in which the observation unit is disposed outside of the optical path, a configuration in which the observation unit is disposed in a backward direction of some members, that is, some members (for example, a flat mirror 12), of the members of the projection optical system may be employed. In this manner, the target light flux is reflected from some members and is transmitted through some members such that it is possible to observe the examinee's eye from the observation unit. For example, in the embodiment, the observation unit is disposed outside of the optical path through which the target light flux passes. Therefore, the observation unit does not block the optical path through which the target light flux passes, and thus it is possible to reduce an occurrence of a defect in the examination target. Hence, it is possible to present an examination target suitable for the examinee's eye.

For example, the observation unit may be configured to include an observation window (for example, an observation window 41) for observing the positional relationship between the eye refractivity measuring unit and the examinee's eye via the presentation window from the outside of the housing. For example, the observation window may be formed by a transparent panel. For example, as a material of the observation window, a transparent member of acrylic resin, a glass plate, or the like may be used.

For example, the observation unit includes the observation window for observing the positional relationship between the eye refractivity measuring unit and the examinee's eye. Therefore, the examiner directly looks into the observation window, thereby making it possible to check the pupil position of the examinee's eye and the position of the eye refractivity measuring unit. The examiner can easily check the pupil position of the examinee's eye and the position of the eye refractivity measuring unit in a simple configuration.

For example, the observation unit may further include a shielding portion (for example, a shielding portion 42) that shields the target light flux emitted from the projection optical system. For example, the observation unit includes the shielding portion for shielding the target light flux. Therefore, the target light flux emitted from the target presenting unit is not guided to the examiner, and thus it is possible to observe the examinee's eye from the observation window without feeling dazzling. Hence, when the examinee checks the target and performs the examination, it is possible to reduce an occurrence of reflection of the target on the observation window and interference with the examination.

For example, the shielding portion may use a member made of various materials (for example, resin or metal). In addition, for example, the shielding portion may be obtained by performing coating or the like for reducing reflection from the various materials. For example, the shielding portion may be disposed at a position at which it is possible to reduce an occurrence of entering of the target light flux emitted from the projection optical system to the observation window.

For example, the observation unit may include a cover (for example, a cover 43) that is openable and closeable with respect to the observation window and detecting means (for example, a detector 45) that detects opening and closing of the cover. In this case, for example, the subjective optometric apparatus further may include controlling means (for example, a controller 80) that performs switching between a first mode for performing subjective examination on the examinee and a second mode for checking the pupil position of the examinee, based on detected results from the detecting means. For example, the detector may use a light sensor (for example, a photointerrupter), a position detecting sensor, a rotating angle sensor, or the like. For example, in this example, the observation unit includes a cover that is openable and closeable with respect to the observation window and the detecting means that detects opening and closing of the cover. In addition, for example, the subjective optometric apparatus includes the controlling means that performs switching between the first mode for performing subjective examination on the examinee and the second mode for checking the pupil position of the examinee, based on the detected results from the detecting means. In this manner, setting for checking the pupil position of the examinee's eye and the position of the eye refractivity measuring unit is manually performed, and thus the examiner can smoothly prepare the subjective examination.

In addition, for example, the observation unit may be configured to include an imaging optical system provided with an imaging element that images the eye refractivity measuring unit and the examinee's eye via the presentation window. For example, the subjective optometric apparatus in this example includes the imaging optical system for imaging the eye refractivity measuring unit and the examinee's eye via the presentation window. In this manner, the examiner can easily check the pupil position of the examinee's eye and the position of the eye refractivity measuring unit in a simple configuration.

For example, the subjective optometric apparatus may include a cornea position alignment optical system (for example, a cornea position alignment optical system 60). In this case, for example, the subjective optometric apparatus may include a checking window (for example, a checking window 65). In this case, for example, the subjective optometric apparatus may include a light guiding unit (for example, a light guiding unit 66). For example, the cornea position alignment optical system is disposed in the eye refractivity measuring unit, and the cornea position alignment optical system is used to check an inter-vertex distance between a lens wearing reference position and a cornea vertex of the examinee's eye. For example, the checking window is used to check the cornea position alignment optical system disposed in the inside of the eye refractivity measuring unit from the outside of the eye refractivity measuring unit. For example, the light guiding unit is used to check the checking window. For example, in this example, the subjective optometric apparatus includes: the cornea position alignment optical system that is disposed in the eye refractivity measuring unit and is used to check the inter-vertex distance between the lens wearing reference position and the cornea vertex of the examinee's eye; a checking window for checking the cornea position alignment optical system disposed in the inside of the eye refractivity measuring unit from the outside of the eye refractivity measuring unit; and a light guiding unit for observing the checking window. In this manner, the examiner can easily check the positional relationship between the eye refractivity measuring unit and a position of the cornea vertex of the examinee's eye and can easily perform the position adjustment between the examinee's eye and the eye refractivity measuring unit.

For example, the cornea position alignment optical system may be provided as both of a cornea position alignment optical system for the left eye and a cornea position alignment optical system for the right eye. In this case, for example, the light guiding unit may be provided as both of a light guiding unit for the left eye and a light guiding unit for the right eye. In addition, for example, the cornea position alignment optical system may be provided as one of the cornea position alignment optical system for the left eye or the cornea position alignment optical system for the right eye. In this case, for example, the light guiding unit may be provided on the side on which the cornea position alignment optical system is provided.

<Light Emitting Means>

For example, the subjective optometric apparatus in the embodiment includes light emitting means (for example, a surface light emitting unit 90). For example, the light emitting means is a member different from the target presenting unit and causes surface light emission to be performed on the periphery of the target presenting unit. For example, the subjective optometric apparatus includes: the projection optical system that has the target presenting unit which emits the target light flux and that projects, onto the examinee's eye, the target light flux emitted from the target presenting unit; the housing that accommodates the projection optical system; and the light emitting means that is a member different from the target presenting unit and causes surface light emission to be performed on the periphery of the target presenting unit. According to such a configuration, it is possible to suppress reduction in retinal illuminance, and it is possible to perform the subjective measurement in a state in which a vision close to a natural vision is obtained.

For example, the light emitting means may be configured to be disposed to surround the target presenting unit on the periphery thereof. For example, the light emitting means is disposed to surround the target presenting unit on the periphery thereof. In this case, for example, the light emitting means may be configured to be disposed to be connected to the target presenting unit. In this case, for example, the light emitting means may be configured to have a separate member in at least a part between the target presenting unit and the light emitting means. In this case, for example, the light emitting means may be configured to have a space in at least a part between the target presenting unit and the light emitting means. In this manner, the light emitting means is disposed to surround the target presenting unit the periphery thereof, and thus it is possible to reduce uneven illumination on the periphery of the target presenting unit. In other words, it is possible to evenly illuminate the periphery of the target presenting unit.

In addition, for example, the light emitting means may be configured to be disposed at least a part of the periphery of the target presenting unit (for example, at least one direction of the rightward, leftward, upward, and downward directions of the target presenting unit). For example, the light emitting means may have a configuration in which at least some members of the light emitting means are disposed at a different position from the periphery of the target presenting unit. In this case, for example, the light emitting means may be configured to be disposed at the position different from the periphery of the target presenting unit and to illuminate the periphery of the target presenting unit. In this case, for example, there may be employed a configuration in which a reflective member is provided on the periphery of the target presenting unit, the reflective member is irradiated with a light flux from a light source provided at a separate position different from the periphery, the reflective member reflects the light flux, and surface light emission is performed from the periphery of the target presenting unit. In this case, for example, there may be employed a configuration in which the inside of the housing is illuminated, and thereby the periphery of the target presenting unit is illuminated and observed when the examinee observes the target presenting unit.

For example, the light emitting means is capable of causing the surface light emission to be performed on the periphery of the target presenting unit at an arbitrary luminance value. For example, the light emitting means may be configured to cause the surface light emission to be performed on the periphery of the target presenting unit at a luminance value to the extent that a state in which a vision is close to the natural vision is obtained. In this case, for example, the light emitting means may be configured to cause the surface light emission to be performed on the periphery of the target presenting unit at a luminance value to the extent that it is possible to suppress the reduction in the retinal illuminance. For example, the light emitting means may be configured to cause the surface light emission to be performed on the periphery of the target presenting unit at a luminance value smaller than a luminance value approximate to the luminance value of the target presenting unit. In this case, for example, the light emitting means may cause the surface light emission to be performed on the periphery of the target presenting unit at a luminance value of 10% to 25% with respect to the luminance value of the target presenting unit. In this manner, the periphery of the target presenting unit gets too bright, and thereby it is possible to reduce glare in the examinee' eye during the subjective examination such that deterioration of measurement accuracy of the subjective examination is reduced. In addition, for example, the periphery of the target presenting unit gets too dark, and thereby an occurrence of a state in which it is not possible to suppress the reduction in retinal illuminance is reduced such that it is possible to perform the subjective measurement in a state in which the vision is close to the natural vision. In this case, for example, the luminance value of the surface light emitting unit 90 has the same level as the luminance value of the target presenting unit, and thereby it may be possible to perform observation in a state in which a background region of the target is broadened when the examiner observes the target. A configuration of the light emitting unit in which the surface light emission is performed on the periphery of the target presenting unit at the luminance value smaller than the luminance value approximate to the luminance value of the target presenting unit includes a configuration in which the luminance value of the light emitting means is slightly larger than the luminance value of the target presenting unit.

For example, the light emitting means may have openings (for example, an opening 97 and an opening 98). For example, the opening may be provided at the central region of the light emitting means. In addition, for example, the opening may be provided in a region (for example, a region in at least one direction of the rightward, leftward, upward, and downward directions) different from the central region of the light emitting means. For example, the target presenting unit may be disposed in the opening. In this manner, the target light flux emitted from the target presenting unit is projected onto the examinee's eye through the opening.

<Example>

Figure 2:
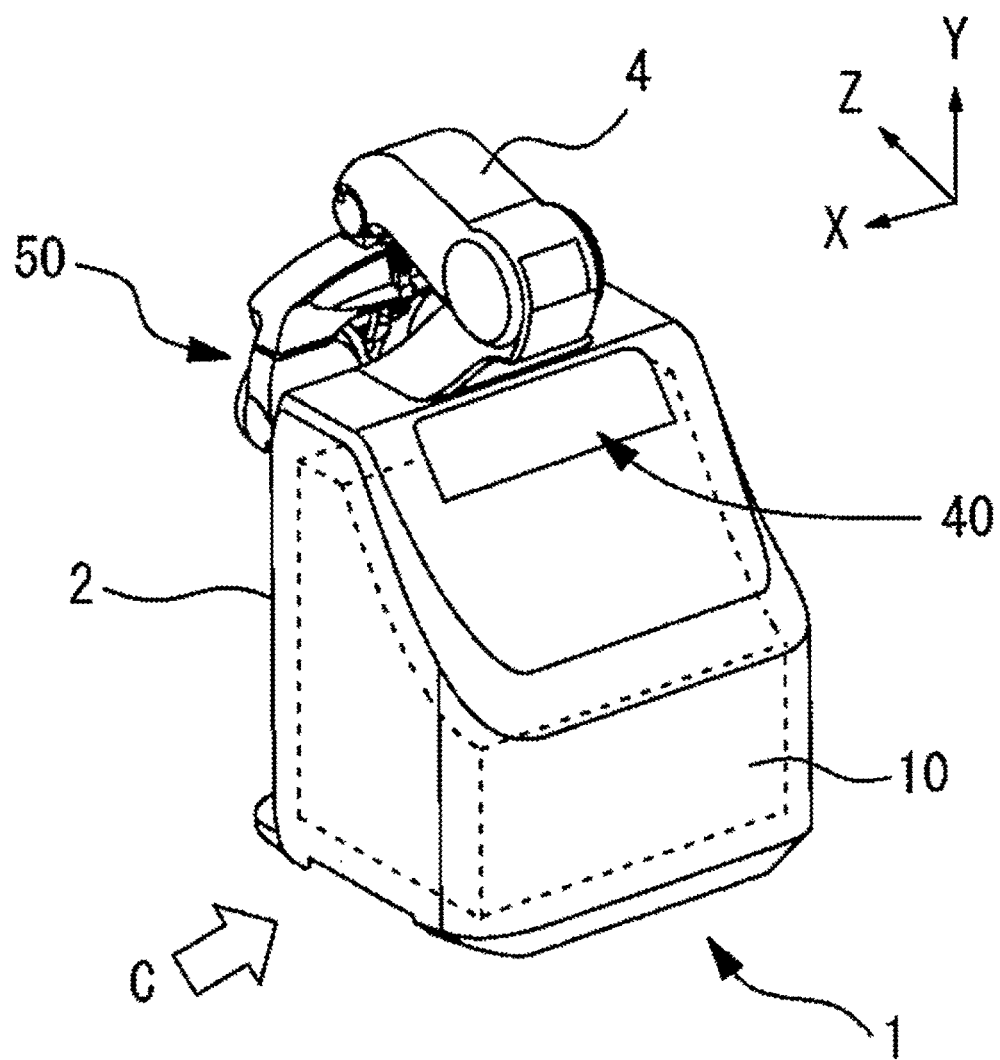
FIG. 2 is a perspective view illustrating the subjective optometric apparatus viewed from a back side.

Hereinafter, a configuration of the subjective optometric apparatus in the example will be described. FIG. 1 is a view illustrating the external appearance of the subjective optometric apparatus 1 according to the example. FIG. 1 is a perspective view illustrating the subjective optometric apparatus 1 viewed from a front side. FIG. 2 is a perspective view illustrating the subjective optometric apparatus 1 viewed from a back side. In the example, a side, on which the presentation window 3 to be described below is positioned, is described as a front surface of the subjective optometric apparatus 1, and a side, on which the observation window 41 to be described below is positioned, is described as a back surface of the subjective optometric apparatus 1.

For example, the subjective optometric apparatus 1 includes the housing 2, the presentation window 3, a holding arm 4, the projection optical system 10, the observation unit 40, the eye refractivity measuring unit 50, and the like.

For example, in the example, the examinee faces the front surface of the housing 2. For example, the housing 2 accommodates the projection optical system 10 in the inside thereof. For example, the presentation window 3 is used to present the examination target to the examinee's eye. For example, the presentation window 3 transmits the target light flux in the projection optical system 10. Therefore, the target light flux is projected onto the examinee's eye via the presentation window 3. For example, the presentation window 3 is blocked with a transparent panel for preventing dust from infiltrating thereinto. For example, as the transparent panel, a transparent member made of acrylic resin, a glass plate, or the like may be used.

In a case where the eye refractivity measuring unit 50 is disposed between the presentation window 3 and the examinee's eye, the target light flux is projected onto the examinee's eye via the presentation window 3 and a test window 53 of the eye refractivity measuring unit 50.

Figure 13:
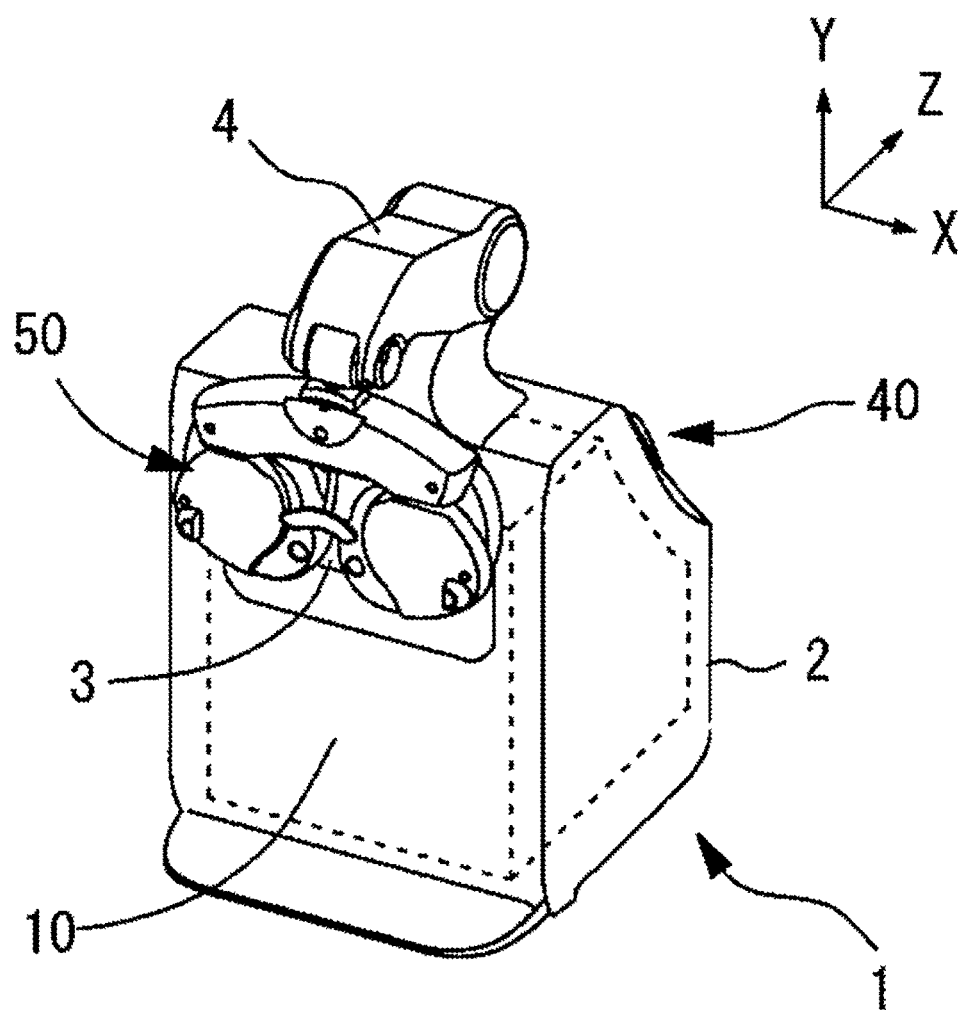
FIG. 13 is a view illustrating a state in which the eye refractivity measuring unit is disposed at a measuring position.

For example, the holding arm 4 holds the eye refractivity measuring unit 50. For example, the holding arm 4 supports the eye refractivity measuring unit 50 at a standby position or a measurement position. For example, as illustrated in FIG. 1, at the standby position in the example, the eye refractivity measuring unit 50 is in a lifted state above the housing 2. In addition, as illustrated in FIG. 13, at the measurement position in the example, the eye refractivity measuring unit 50 is in a lowered state on the front surface of the housing 2. Switching between the standby position and the measurement position is performed by a drive unit 6 to be described below causing the holding arm 4 to move up and down.

Figure 3:
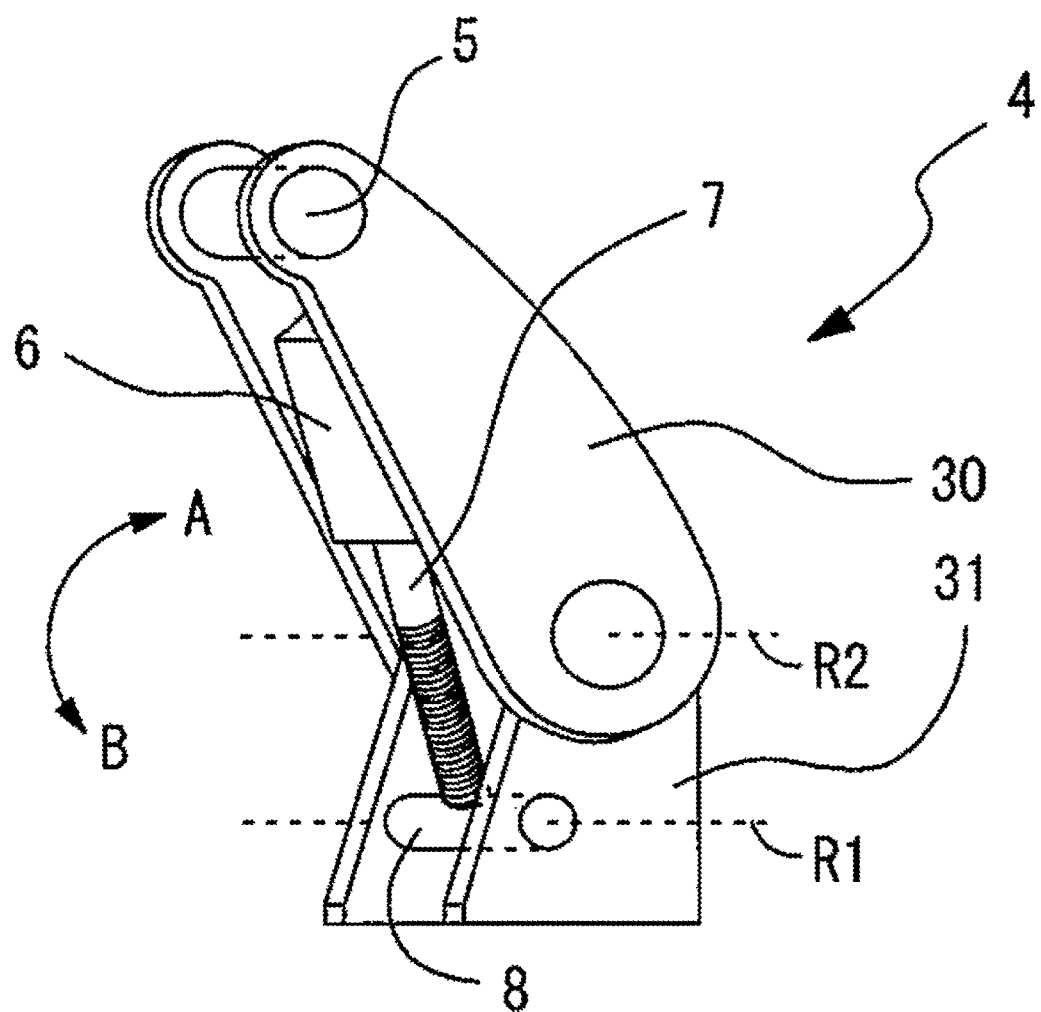
FIG. 3 is a view illustrating a state in which a cover of a holding arm is detached.

For example, FIG. 3 is a view illustrating a state in which a cover of the holding arm 4 is detached. For example, the holding arm 4 is configured to include the drive unit (for example, a motor) 6, an arm portion 30, a base stand 31, and the like. For example, the holding arm 4 includes a connecting portion 5. For example, the holding arm 4 and the eye refractivity measuring unit 50 are connected to each other via the connecting portion 5. For example, the arm portion 30 is attached to the base stand 31. For example, the base stand 31 is provided on the top surface of the housing 2. For example, the motor 6, a shaft 7, a support member 8, and the like are provided. For example, the motor 6 is fixed to the arm portion 30 and is connected to an upper portion of the shaft 7. For example, a lower portion of the shaft 7 is provided with a threaded portion and is screwed into the support member 8. For example, the support member 8 is attached to the base stand 31. For example, the support member 8 supports the shaft 7 in a rotatable manner in the upward-downward direction with respect to the base stand 31 around a rotation axis R1. For example, the base stand 31 is disposed to be fixed to the housing 2.

For example, in the example, the motor 6 performs driving, thereby rotating the shaft 7 in a helical direction of the threaded portion. In this manner, the shaft extends and retracts with respect to the support member 8. For example, when the shaft 7 extends, the support member 8 rotates around the rotation axis R1 in an arrow A direction. At this time, the motor 6 connected to the shaft 7 and the arm portion 30, to which the motor 6 is fixed, rotate integrally around a rotation axis R2 in the arrow A direction. In addition, for example, when the shaft 7 retracts, the support member 8 rotates around the rotation axis R1 in an arrow B direction. At this time, the motor 6 connected to the shaft 7 and the arm portion 30, to which the motor 6 is fixed, rotate integrally around the rotation axis R2 in the arrow B direction. For example, the holding arm 4 can move up and down with respect to the housing 2 in such a manner in the example, and the eye refractivity measuring unit 50 fixed to the holding arm 4 can move to the standby position and the measurement position. In other words, the eye refractivity measuring unit 50 can switch between the standby position and the measurement position.

<Projection Optical System>

Figure 4A:
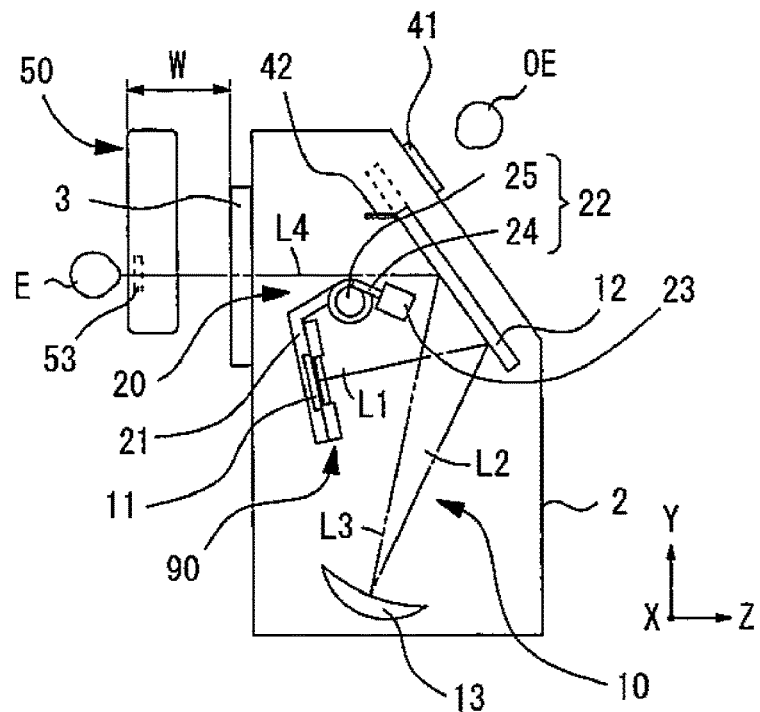
FIGS. 4A and 4B are views illustrating a projection optical system viewed from a right side.
Figure 4B:
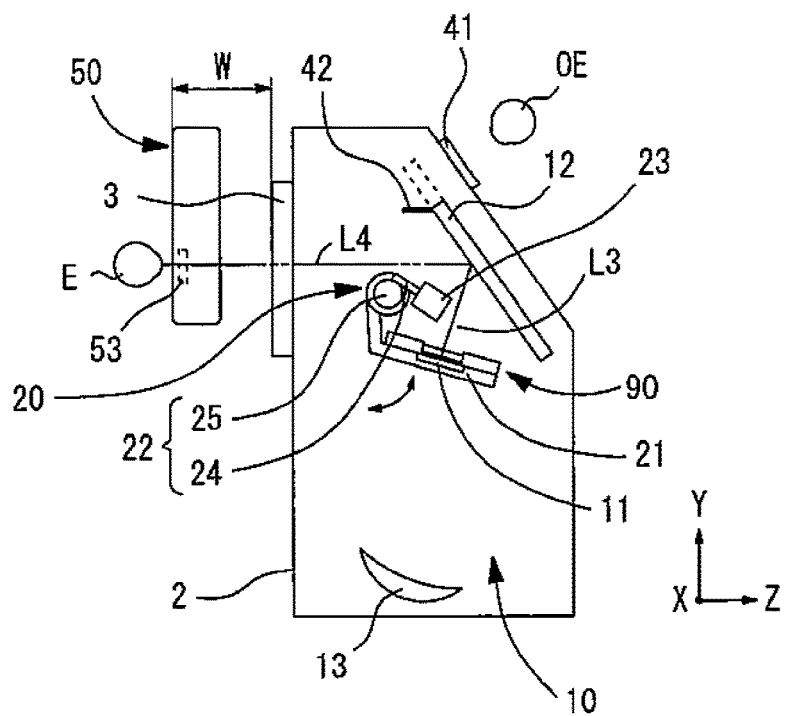

Hereinafter, the projection optical system 10 will be described. For example, FIG. 4 is a view illustrating the projection optical system 10 viewed from a right side (an arrow direction C in FIGS. 1 and 2). FIG. 4(a) illustrates optical disposition during a distance vision examination. FIG. 4(b) illustrates optical disposition during a near vision examination. For example, the projection optical system 10 has the target presenting unit and projects, onto an examinee's eye E, the target light flux emitted from the target presenting unit. For example, in the example, the display (for example, the display 11) is used as the target presenting unit. For example, the projection optical system 10 includes the display 11, the flat mirror 12, a concave mirror 13, a distance/near vision switching unit 20, and the like.

For example, the examination target such as a Landolt ring target or a fixation target is displayed on the display 11. For example, a controller 80 to be described below controls a display on the display 11. For example, the liquid crystal display (LCD), an organic electroluminescence (EL), a plasma display, or the like is used as the display.

For example, during the distance vision examination illustrated in FIG. 4(a), a screen on the display 11 faces a deep side of the housing 2 and the target light flux is emitted in the depth direction. The target light flux may be emitted in a horizontal direction (Z direction) or may be emitted in an oblique direction (YZ direction) from the display. For example, during the near vision examination illustrated in FIG. 4(b), the screen on the display 11 faces an upper side and the target light flux is emitted in the upward direction. The target light flux may be emitted in a perpendicular direction (Y direction) or may be emitted in the oblique direction (YZ direction) from the display. In this manner, the target light flux from the display 11 is projected onto the examinee's eye E.

For example, the flat mirror 12 reflects the target light flux emitted from the display 11 and guides the target light flux to the concave mirror 13. In addition, for example, the flat mirror 12 reflects the target light flux emitted from the display 11 and guides the target light flux to the examinee's eye E. For example, the flat mirror 12 is subjected to the mirror coating only on a lower portion (solid-line portion of the flat mirror 12 in FIG. 4), and the upper portion (dotted-line portion of the flat mirror 12 in FIG. 4) is not subjected to the mirror coating.

Therefore, in the example, the upper portion of the flat mirror 12 is configured to be transparent. For example, a focal length of the flat mirror 12 during the near vision examination is set such that an optical path length from the display to the examinee's eye E is 40 cm. In the example, the flat mirror may be any member that is capable of reflecting the target light flux, and the example is not limited to the configuration of using the flat mirror. For example, a reflective member may be used. In this case, for example, a configuration of using a prism, a beam splitter, a half mirror, or the like may be employed.

For example, the concave mirror 13 reflects, to the flat mirror 12, the target light flux emitted from the display 11. For example, the concave mirror 13 sets, to a distance vision examination length, a presentation length of the examination target displayed on the display 11. For example, a focal length of the concave mirror 13 is set such that an optical path length from the display 11 to the examinee's eye E is 5 m. The example is not limited to the configuration of using the concave mirror 13. For example, the concave mirror may be a reflective member that is capable of reflecting the target light flux. In this case, for example, a configuration of using an aspherical mirror, a free-form surface mirror, or the like may be employed. In addition, for example, a configuration of using a lens may be employed. In this case, for example, the target light flux is projected on the examinee's eye E via the lens from the display 11, and thereby a configuration in which the optical path length from the display 11 to the examinee's eye E is set to 5 m may be employed.

For example, during the distance vision examination illustrated in FIG. 4(a), the target light flux is emitted from the display 11 and is projected on the examinee's eye E through optical members of the flat mirror 12, the concave mirror 13, and the flat mirror 12, in this order. In other words, when the target light flux emitted from the display 11 is incident to the flat mirror 12 through an optical axis L1, the target light flux is reflected in an optical axis L2 direction and travels toward the concave mirror 13. When the target light flux is incident to the concave mirror 13, the target light flux is reflected in an optical axis L3 direction and travels toward the flat mirror 12. Further, when the target light flux is incident to the flat mirror 12, the target light flux is reflected in an optical axis L4 direction and is projected on the examinee's eye E. In addition, for example, during the near vision examination illustrated in FIG. 4(b), the target light flux is emitted from the display 11, reflected from the flat mirror 12, and projected on the examinee's eye E. In other words, when the target light flux emitted from the display 11 is incident to the flat mirror 12 through an optical axis L3, the target light flux is reflected in the optical axis L4 direction and is projected on the examinee's eye E. For example, in this manner, the projection optical system 10 outputs the target light flux from the inside to the outside of the housing 2.

For example, during the distance vision examination and the near vision examination, the distance/near vision switching unit 20 changes the position of the display 11. For example, the distance/near vision switching unit 20 includes a holder 21, a gear 22, a motor 23, and the like. For example, the holder 21 holds the display 11. For example, the gear 22 has a worm 24 and a wheel 25. For example, the worm 24 and the wheel 25 are formed into gears which mesh with each other. For example, the motor 23 is connected to the worm 24, and the holder 21 is connected to the wheel 25. For example, the motor 23 performs driving, thereby rotating the worm 24, and the wheel 25 is rotated in an arrow direction along with the rotation of the worm. In this manner, it is possible to cause the display 11 and the holder 21 to integrally move, and thus it is possible to switch between the measurement positions of the examination target displayed on the screen of the display 11 between during the distance vision examination and during the near vision examination. The gear 22 and the motor 23 are disposed on a side wall of the housing 2 and are disposed at positions at which the gear and the motor do not interfere with the target light flux from the display 11 toward the examinee's eye E.

<Observation Unit>

Figure 5:
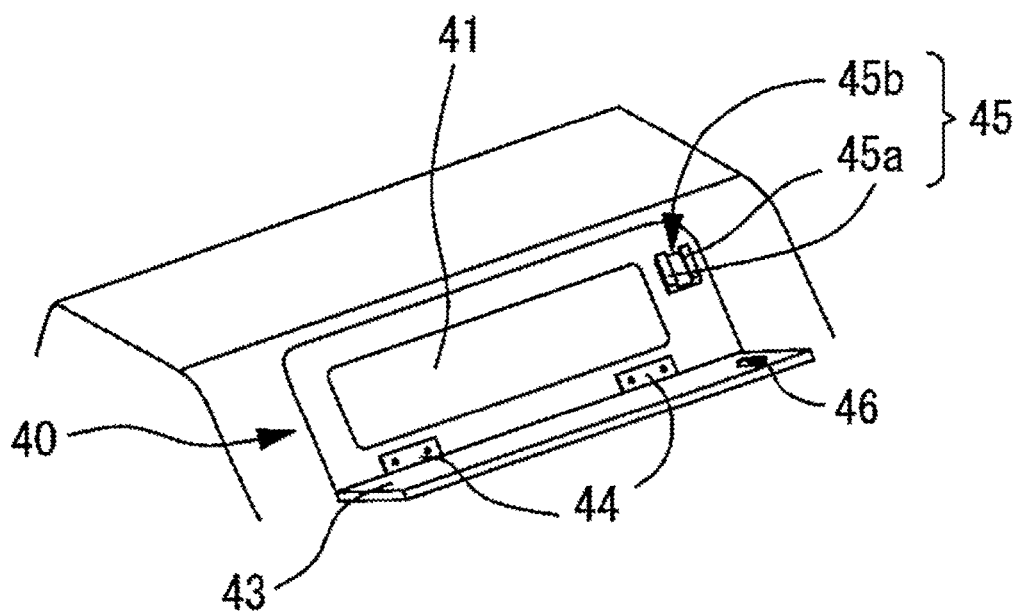
FIG. 5 is a view for describing an observation unit.

Hereinafter, the observation unit 40 will be described. For example, FIG. 5 is a view illustrating an example of the observation unit 40. For example, in the example, the observation unit 40 is used to observe a positional relationship between the eye refractivity measuring unit 50 to be described below and the examinee's eye E via the presentation window 3. For example, in the example, the observation unit 40 includes the observation window 41, the shielding portion 42 (refer to FIG. 4), the cover 43, a detector (detecting means) 45, and the like. The observation unit 40 may be configured to include at least the observation window 41.

For example, the observation window 41 is used to observe the positional relationship between the eye refractivity measuring unit 50 and the examinee's eye E via the presentation window 3 from the outside of the housing 2. For example, in the example, the observation window 41 is disposed at a position at which it is possible to check a pupil position C (for example, refer to FIG. 14) of the examinee's eye E from an examiner's eye OE. For example, the examiner looks into the observation window 41, thereby making it possible to check both of the pupil positions C of the examinee's right and left eyes E. In this manner, for example, it is possible to perform the position adjustment of the examinee's right and left eyes E to positions of right and left test windows 53 of the eye refractivity measuring unit. For example, during the position adjustment between the examinee's eyes E and the test windows 53, lenses provided with a cross mark for position adjustment are positioned on the right and left test windows 53. For example, the central position F (refer to FIG. 14) of the cross mark and the pupil position C of the examinee's eye are subjected to the position adjustment, and thereby it is possible to perform the position adjustment. The detailed description thereof will be provided below.

For example, the observation window 41 is disposed outside of an optical path through which the target light flux of the projection optical system 10 passes (refer to FIG. 4). The observation window 41 is disposed outside of the optical path, and thereby the examination target displayed on the display 11 is presented to the examinee's eye E without a defect. For example, in the example, the observation window 41 is disposed above the optical path of the target light flux, thereby being disposed outside of the optical path.

For example, the observation window 41 is blocked with a transparent panel for preventing dust from infiltrating thereinto. For example, as the transparent panel, a transparent member made of acrylic resin, a glass plate, or the like may be used. For example, in the example, the observation window 41 is configured of the transparent panel. Further, as described above, the configuration in which the upper portion (dotted-line portion) of the flat mirror 12 included in the projection optical system 10 is transparent is employed. For example, in a case where the examiner looks into the observation window 41, the flat mirror 12 is formed to be transparent in a region through which a visual field of the examiner passes such that the flat mirror 12 does not block the visual field of the examiner. According to such a configuration described above, the examiner (examiner's eye OE) can observe the examinee's eye E from the back side of the housing 2 via the observation window 41 and the flat mirror 12.

In the example, the configuration in which a part of the flat mirror 12 is transparent is described as an example; however, the example is not limited thereto. For example, there may be employed a configuration in which the flat mirror 12 has a size to the extent that the flat mirror 12 is not positioned in a region through which the visual field of the examiner passes. In addition, for example, the position, at which the flat mirror 12 is disposed, may be set such that the flat mirror 12 is not positioned in the region through which the visual field of the examiner passes. In this case, there is employed a configuration, during the observation of the examinee's eye E from the observation window 41, the observation window 41 is positioned at a position at which the flat mirror 12 does not block the visual field of the examiner's eye OE. In addition, there is employed a configuration, during the observation of the examinee's eye E from the observation window 41, the flat mirror is disposed at a position at which the flat mirror 12 does not block the visual field of the examiner's eye OE.

For example, the shielding portion 42 shields the target light flux emitted from the projection optical system 10. For example, the target light flux from the projection optical system 10 is internally reflected in the inside of the housing 2 and enters the observation window 41, in some cases. In addition, for example, a target light flux traveling in a direction toward the observation window 41 of the target light fluxes from the projection optical system 10 enters the observation window 41 in some cases. In such a case, when the examiner looks into the observation window 41, the examiner has glare in his or her eyes and does not appropriately perform the observation in some cases. In addition, in such a case, when the examinee checks the target and performs the examination, the target is reflected on the observation window 41 and interference with the examination occurs in some cases. For example, the shielding portion 42 reduces an amount of the target light flux emitted from the projection optical system 10, which enters the observation window 41. For example, as the shielding portion 42, a member made of aluminum subjected to black coating is used. It is needless to say that the shielding portion 42 is not limited to such a configuration described above. For example, the shielding portion 42 may be configured to reduce an amount of the target light flux emitted from the projection optical system 10, which enters the observation window 41. For example, the shielding portion 42 may use a member made of various materials (for example, resin or metal). In addition, the shielding portion 42 may be obtained by performing coating or the like for reducing reflection from the various materials.

For example, the shielding portion 42 is disposed on an upper side of the flat mirror 12. In addition, for example, the shielding portion 42 is on a lower side of the observation window 41 inside the housing 2. For example, in the example, the shielding portion 42 is disposed on a boundary between the transparent portion and the mirror portion of the flat mirror 12. The position, at which the shielding portion 42 is disposed, is not limited to the configuration described above. For example, the shielding portion 42 may be disposed at a position at which it is possible to reduce an occurrence of entering of the target light flux emitted from the projection optical system 10 to the observation window 41.

As described above, in the example, the shielding portion 42 is provided, and thereby, during the distance vision examination illustrated in FIG. 4(a), an amount of the target light flux traveling in the direction toward the observation window 41 of the target light fluxes from the projection optical system 10 is suppressed from being projected on the examiner's eye OE.

For example, the cover 43 is fixed to the housing 2 with a hinge 44, and thereby the cover can be openable and closeable with respect to the observation window 41. For example, the examiner can open or close the cover 43 by pushing or pulling a knob not illustrated. The opening and closing of the cover 43 is not limited to the example. The cover 43 may have a configuration in which the examiner can put his or her hand through the cover 43. In this case, for example, there is employed a configuration or the like in which a cutout is provided in the cover 43.

For example, the detector 45 detects the opening/closing of the cover 43 in the observation unit 40. For example, the detector 45 is configured to have a light sensor such as a photointerrupter. In other words, the detector 45 in the example has a light emitting element and a projection portion 45a that is opposite to the light emitting element, and a protruding portion 46 provided on the cover 43 is fitted into a recessed portion 45b. For example, when the protruding portion 46 is fitted into the recessed portion 45b, and thereby the light from the light from the light emitting element is blocked, the detector 45 detects that the cover is in a closed state. In addition, for example, when the protruding portion 46 is separated from the recessed portion 45b, and the light from the light emitting element is received by a light receiving element, the detector 45 detects that the cover is in an open state. In the example, the configuration in which the photointerrupter is used as the detector 45 is described as an example; however, the example is not limited thereto. The detector 45 may be configured to detect the opening/closing of the cover 43. For example, it is possible to use a position detecting sensor, a rotating angle sensor, or the like as the detector.

<Eye Refractivity Measuring Unit>

Hereinafter, the eye refractivity measuring unit 50 will be described. For example, the eye refractivity measuring unit 50 is close to the housing 2 (refer to FIG. 4). For example, in the example, a length W (refer to FIG. 4) from the test window 53 in the eye refractivity measuring unit 50 to the presentation window 3 disposed in the housing 2 is set to about 135 mm. The length W from the test window 53 to the presentation window 3 is not limited to the example. For example, in a case where the length W is shorter than a length of the examiner' head, it is not possible for the examiner to put his or her head between the eye refractivity measuring unit 50 and the housing 2. Therefore, it is difficult to observe the positional relationship between the eye refractivity measuring unit 50 and the examinee's eye E. Therefore, in a case where the length W is shorter than the length of the examiner's head, it is possible to effectively use the observation window 41.

Figure 6:
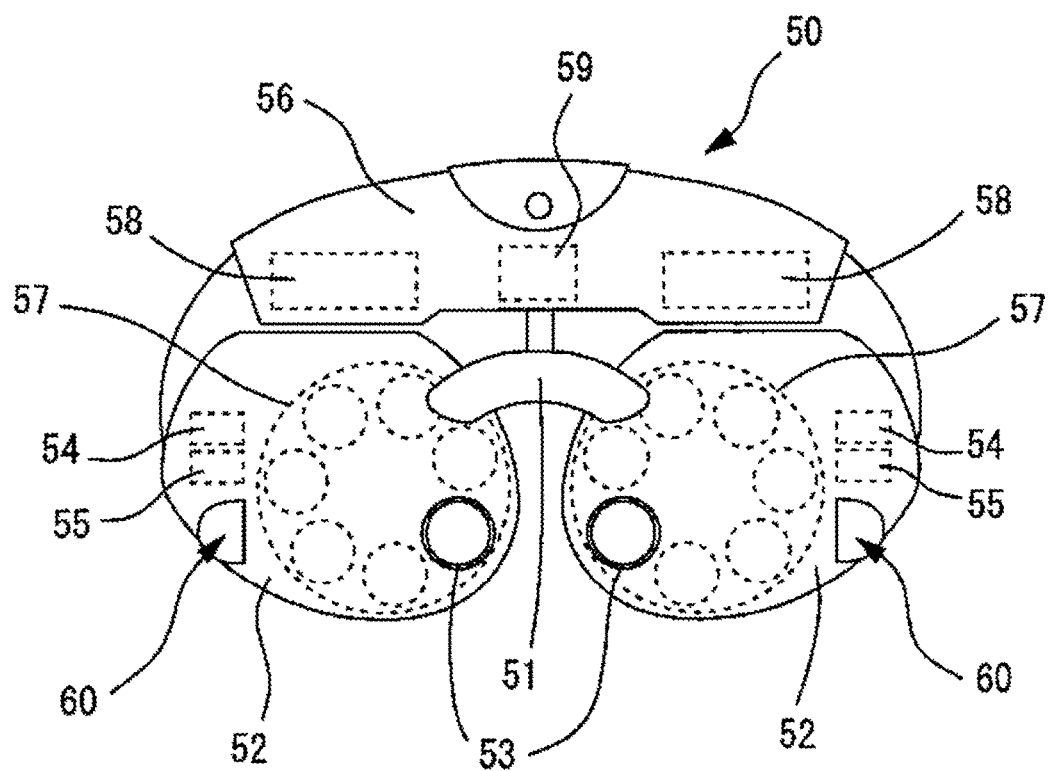
FIG. 6 is a view illustrating an eye refractivity measuring unit.

For example, FIG. 6 is a view illustrating the eye refractivity measuring unit 50. For example, the eye refractivity measuring unit 50 includes a forehead rest 51, a pair of right and left lens chamber units 52, the test windows 53, drive units 54, drive units 55, a moving unit 56, the cornea position alignment optical system 60, and the like. For example, the forehead rest 51 abuts on the forehead of the examinee and is used to constantly maintain a distance between the examinee's eye E and the eye refractivity measuring unit 50.

For example, the lens chamber unit 52 disposes the optical elements in the test window 53 in a switchable manner. For example, a lens disc 57 is provided in the inside of the lens chamber unit 52. The lens disc 57 is used to dispose multiple optical elements (a spherical lens, a cylinder lens, a dispersing prism, and the like) on the same circumference. For example, the lens disc 57 is rotated and controlled by the drive unit 54 (actuator or the like). In this manner, an optical element desired by the examiner is disposed in the test window 53. For example, the optical element disposed in the test window 53 is rotated and controlled by the drive unit 55 (motor, solenoid, or the like). In this manner, the optical element is disposed in the test window 53 at a rotating angle desired by the examiner.

For example, the lens disc 57 is formed by one lens disc or a plurality of lens discs. For example, in a case where the plurality of lens discs (a lens disc group) are included, drive units corresponding to the respective lens discs are provided. For example, the lens discs of the lens disc group include an opening (or a lens of OD) and a plurality of optical elements. Types of the lens discs representatively include a spherical lens disc having a plurality of spherical lenses having different powers, a cylinder lens disc having a plurality of cylinder lenses having different powers, and an auxiliary lens disc. In addition, the lens disc in the example includes a lens (refer to FIG. 14) for position adjustment which is provided with a cross line (detailed description thereof below). For example, on the auxiliary lens disc, at least one of a red filter/green filter, a prism, a cross cylinder lens, a polarizer, a Maddox lens, an auto cross cylinder lens is disposed. Regarding a detailed configuration of the lens disc, refer to JP-A-2007-68574 and JP-A-2011-72431.

For example, the moving unit 56 adjusts a distance between the lens chamber units 52. For example, the distance between the right and left lens chamber units is adjusted by a drive unit 58 having a sliding mechanism. In this manner, a distance between the test windows 53 can be changed depending on PD of the examinee's eyes. In addition, the moving unit 56 adjusts a convergence angle (inside angle) between the right and left lens chamber units. For example, the convergence angle between the right and left eye refractivity measuring units is adjusted by a drive unit 59 having a convergence mechanism. Regarding a detailed configuration of the moving unit, refer to JP-A-2004-329345.

The eye refractivity measuring unit 50 is not limited to the configuration described above. For example, the eye refractivity measuring unit 50 may be configured to change the optical property of the target light flux (for example, at least one of a spherical diopter power, a cylindrical power, a cylindrical axis, a polarization property, and an aberration amount). For example, a configuration of controlling an optical element may be employed as a configuration of changing the optical property of the target light flux. For example, a configuration of using a wavefront modulation element may be employed.

<Cornea Position Alignment Optical System>

Figure 7:
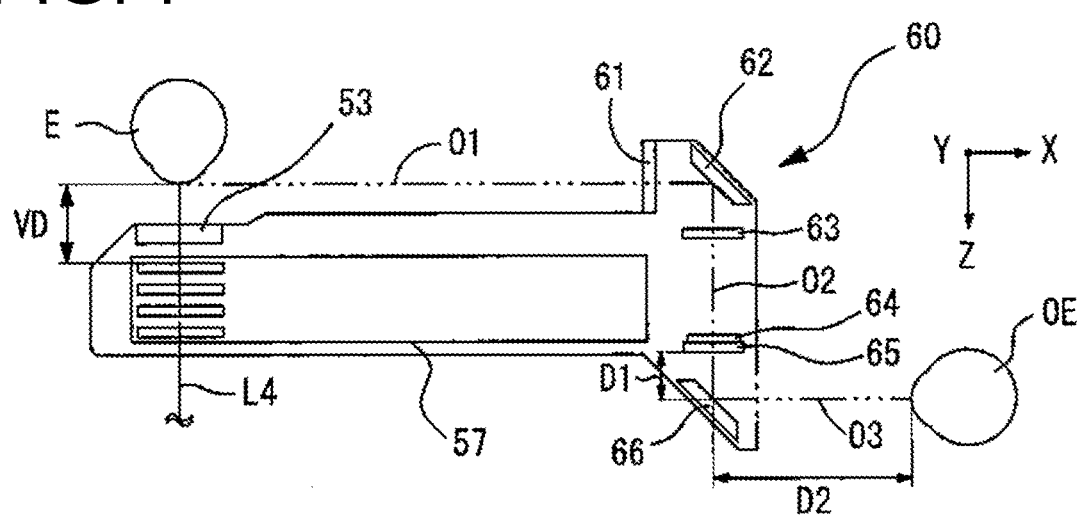
FIG. 7 is a view illustrating a cornea position alignment optical system.

Hereinafter, the cornea position alignment optical system 60 will be described. FIG. 7 is a view illustrating the cornea position alignment optical system 60. For example, the cornea position alignment optical system 60 is disposed inside the eye refractivity measuring unit 50 and is provided in each of the lens chamber units 52. The cornea position alignment optical system 60 has the same configuration in the right side and left side lens chamber units, and thus only the left side lens chamber unit in the example is described.

For example, the cornea position alignment optical system 60 is used to check an inter-cornea vertex distance VD between of the examinee's eyes E and a reference position during the lens wearing to be described below. For example, the cornea position alignment optical system 60 includes an observation light transmitting window 61, a reflective mirror 62, an aiming scale plate 63, a reticle plate 64, a checking window 65, the light guiding unit 66, and the like.

For example, the observation light transmitting window 61 is a window for transmitting the observation light of the examinee's eye E. For example, the reflective mirror 62 is disposed in a side direction (X direction) of the examinee's eye E. For example, the aiming scale plate 63 is provided between the reflective mirror 62 and the checking window 65. The aiming scale plate 63 may be provided between the examinee's eye E and the reflective mirror 62. For example, the reticle plate 64 is disposed on the back side of the checking window 65 (on the inside of the lens chamber unit). For example, the checking window 65 is used to observe the objection light of the examinee's eye E which is projected on the cornea position alignment optical system 60, from the outside of the eye refractivity measuring unit 50. For example, the light guiding unit 66 is used to check the checking window 65. For example, the light guiding unit 66 guides the observation light from the checking window 65 to the outside of the eye refractivity measuring unit 50. For example, the light guiding unit 66 in the example is configured of a mirror.

For example, the observation light from the examinee's eye E is transmitted through the observation light transmitting window 61 and is reflected from the reflective mirror 62 in an optical axis O2 direction from an optical axis O1. The observation light travels toward the light guiding unit 66 via the aiming scale plate 63, the reticle plate 64, and the checking window 65 and is reflected from the light guiding unit 66 in an optical axis O3 direction. In this manner, the examiner's eye OE observes the light guiding unit 66, thereby observing the side of the examinee's eye E.

Figure 8A:
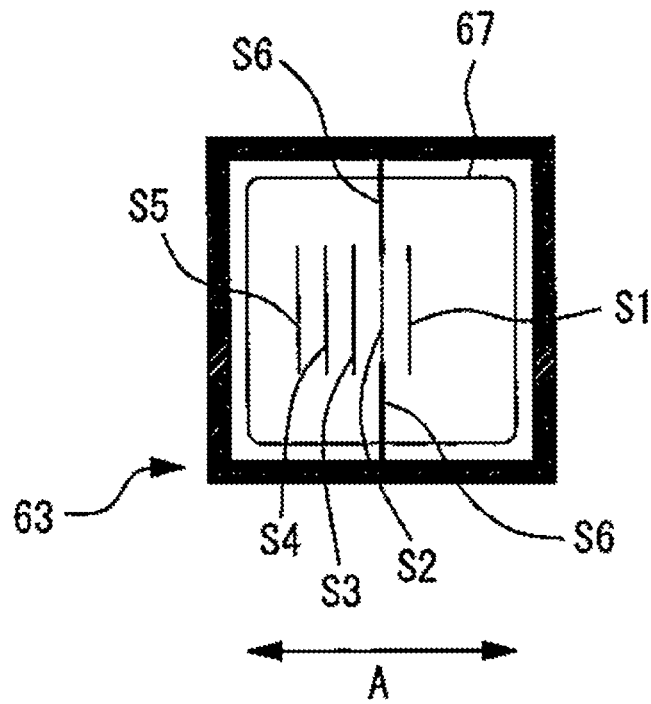
FIGS. 8A and 8B are views of configurations of aiming scale plate and a reticle plate.
Figure 8B:
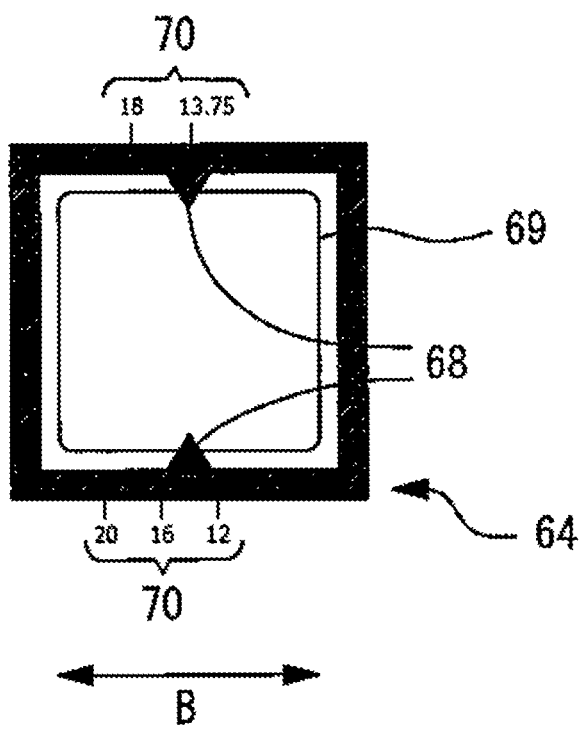

For example, FIG. 8 is a view of configurations of the aiming scale plate 63 and the reticle plate 64. FIG. 8(a) illustrates the aiming scale plate 63, and FIG. 8(b) illustrates the reticle plate 64. For example, the aiming scale plate 63 is provided with several scale lines S1 to S5, the center line S6, and a first mark 67. For example, the scale lines S1 to S5 correspond to VD=12 mm, 13.75 mm, 16 mm, 18 mm, and 20 mm in this order. For example, the scale line S2 (13.75 mm) represents a reference position during the lens wearing and is drawn to be distinguished from the other scale lines. For example, the center line S6 is used as a reference for position adjustment of a reticle 68 on the reticle plate 64. In addition, for example, the center line S6 is positioned at the center of the aiming scale plate 63 in the rightward-leftward direction. For example, the first mark 67 is a mark for guiding the examiner's eye OE at a predetermined distance with respect to the reticle plate 64. In the example, the first mark 67 is formed in a rectangular frame line. For example, the frame line in the first mark 67 is set to a predetermined dimension A in advance.

For example, the reticle plate 64 is provided with the reticle 68, a second mark 69, and the like. For example, the reticle 68 is formed in a triangular shape. In addition, the reticle 68 is positioned at the center of the reticle plate 64 in the rightward-leftward direction. For example, the second mark 69 is a mark for guiding the examiner's eye OE at a predetermined distance with respect to the reticle plate 64 and is used along with the first mark 67 on the aiming scale plate 63. In the example, similar to the first mark 67, the second mark 69 is formed in the rectangular frame line. For example, the frame line in the second mark 69 is set to a predetermined dimension B in advance. For example, a numerical value 70 representing VD is shown in an outer circumferential region of the reticle plate 64.

Figure 9:
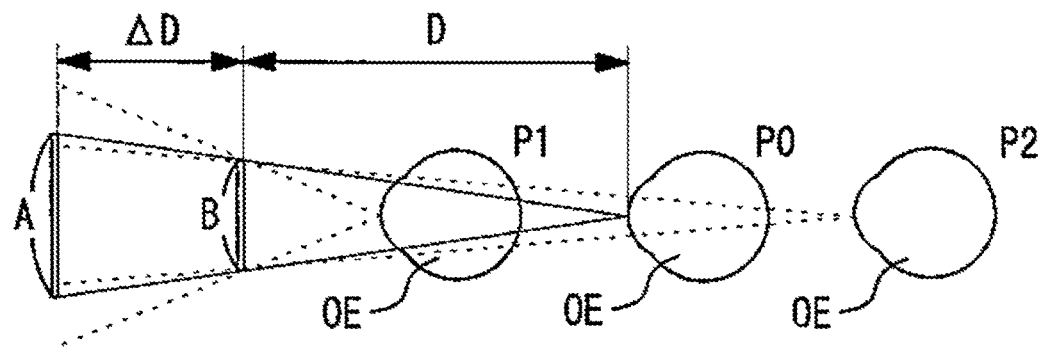
FIG. 9 is a diagram for describing a relationship between a first mark and a second mark.

For example, FIG. 9 is a diagram for describing a relationship between the first mark 67 and the second mark 69. For example, in a case where a distance D obtained by adding a distance D1 (refer to FIG. 8) from the reticle plate 64 to the light guiding unit 66 and a distance D2 (refer to FIG. 8) from the light guiding unit 66 to the examiner's eye OE is 250 mm, the first mark 67 and the second mark 69 are viewed to overlap each other as one. In other words, in the example, by using a distance ΔD from the first mark 67 to the second mark 69 and a design distance D from the second mark 69 to a position at which the examiner's eye OE needs to be disposed, a dimension A of the first mark 67 and a dimension B of the second mark 69 are set to satisfy the following expression.

$$D/(D+\Delta D)=B/A \qquad \text{Expression (1)}$$

For example, in a case where the examiner's eye OE is positioned at P1 closer to the distance D of 250 mm, the first mark 67 is considered to be positioned on an inner side with respect to the second mark 69. In addition, in a case where the examiner's eye OE is positioned at P2 away from the distance D of 250 mm, the first mark 67 is considered to be positioned on an outer side with respect to the second mark 69. For example, when the first mark 67 and the second mark 69 are disposed at a position at which the marks are viewed to overlap each other, the examiner's eye OE is accurately positioned at P0 at which the distance D is 250 mm.

<Surface Light Emitting Unit>

For example, in the example, the light emitting means is provided as a member different from the target presenting unit and causes surface light emission to be performed on the periphery of the target presenting unit. To be more specific, in the example, the subjective optometric apparatus 1 includes the surface light emitting unit 90. For example, the surface light emitting unit 90 is disposed to surround the display 11 the periphery thereof.

Figure 10:
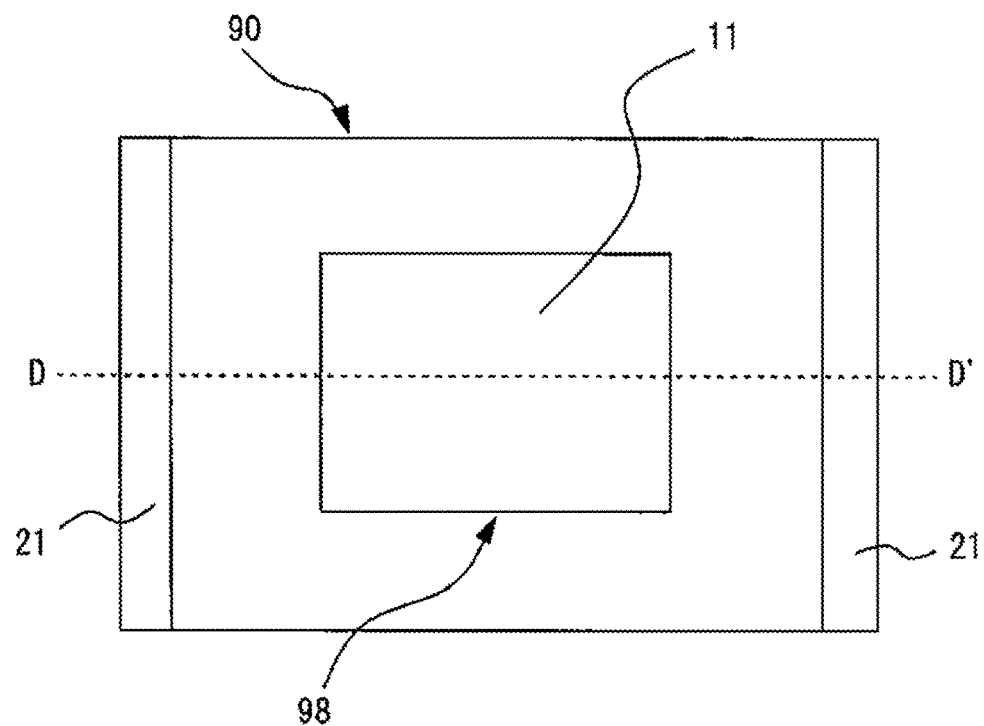
FIG. 10 is a view illustrating a surface light emitting unit viewed in a front direction.
Figure 11:
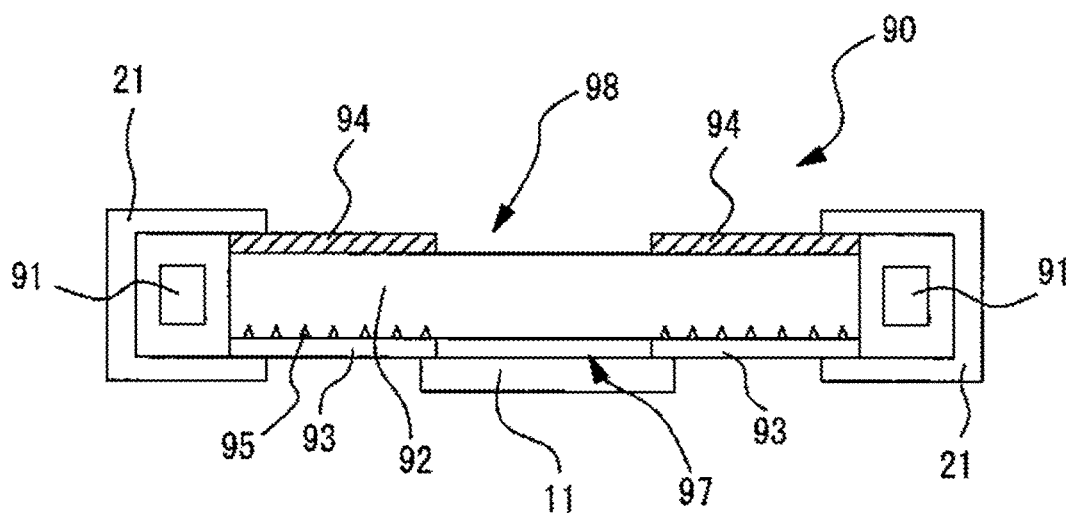
FIG. 11 is a cross-sectional view illustrating a case where the surface light emitting unit and a display are cut.

For example, the surface light emitting unit 90 causes surface light emission to be performed on the periphery of the display 11. Hereinafter, a configuration of the surface light emitting unit 90 will be described. For example, FIG. 10 is a view illustrating the surface light emitting unit viewed in a front direction. For example, FIG. 11 is a sectional view illustrating a case where the surface light emitting unit 90 and the display 11 in FIG. 10 are cut along D-D'.

For example, the surface light emitting unit 90 is configured of a member separate from the display 11. For example, the surface light emitting unit 90 includes a light source 91, a light guiding plate 92, a reflective sheet 93, a diffusion sheet 94, and the like. For example, the surface light emitting unit 90 is held along with the display 11 by the holder 21. For example, the light guiding plate 92 has one surface on which the reflective sheet 93 is disposed and the other surface on which the diffusion sheet 94 is disposed. For example, the display 11 is disposed on the surface on the side on which the reflective sheet 93 is disposed. For example, the reflective sheet 93 is provided with the opening 97 for transmitting the target light flux emitted from the display 11. For example, the light flux from the light source 91 is emitted from the surface on a side, on which the diffusion sheet 94 is disposed, toward the flat mirror 12. In addition, for example, the diffusion sheet 94 is provided with the opening 98 for transmitting the target light flux emitted from the display 11.

For example, in the example, the opening 97 and the opening 98 are formed in the central region of the surface light emitting unit 90. It is needless to say that the openings may be formed in another region. For example, the opening 97 and the opening 98 are formed to have a size to the extent that the target light flux from the display 11 is not shielded. For example, the opening 97 and the opening 98 are formed to have a size equal to or larger than that of the screen of the display 11. For example, it is needless to say that the opening 97 and the opening 98 may be formed to have the size to the extent that the target light flux from the display 11 is not shielded.

For example, as the light sources 91, a light emitting diode (LED), a laser, a halogen lamp, or the like can be used. For example, the light sources 91 are held by the holder 21. For example, a plurality of the light sources 91 are disposed to be adjacent to each other in the upward-downward direction on the paper surface of FIG. 10. It is needless to say that the light sources 91 may be light sources formed into a line shape. For example, the light sources 91 may all be provided in the rightward-leftward direction. For example, both of the right and left light sources 91 emit the light fluxes in a direction to the display 11. It is needless to say that the light sources 91 may have a configuration in which at least one light source is provided. In addition, for example, the positions, at which the light sources 91 are disposed, are not limited thereto in the rightward-leftward direction described above. For example, there may be employed a configuration in which the light sources 91 are disposed on one side in the rightward-leftward direction. In addition, for example, the light source 91 may be disposed in the upward-downward direction.

For example, the light guiding plate 92 diffuses the light flux emitted from the light source 91 and guides the light flux in a direction to the display 11. For example, the light guiding plate 92 guides the light flux emitted from the right and left light sources 91 in the direction to the display 11. For example, the light guiding plate 92 transmits the target light flux emitted from the display 11. For example, the light guiding plate 92 is an acrylic plate formed by using the acrylic resin. For example, the light guiding plate 92 is formed to have a thickness of 2 mm. It is needless to say that the light guiding plate 92 may be formed to have a different thickness. The material of the light guiding plate 95 is not limited to the acrylic resin. Any material may be used as long as the material can guide the light flux emitted from the light source 91.

For example, the light guiding plate 92 is provided with plurality of grooves 95. For example, the grooves 95 are formed in the surface on the side on which the reflective sheet 93 is disposed. For example, the grooves 95 are formed in the light guiding plate 92 by a laser. It is needless to say that the grooves 95 may be formed in the light guiding plate 92 through another method. For example, the light guiding plate 92 may be molded such that the grooves 95 are formed in the light guiding plate 92. For example, some light fluxes of the light fluxes that are emitted from the light source 91 in the direction toward the display 11 are reflected from the grooves 95 and diffused. In the example, as a configuration in which some light fluxes of the light fluxes that are emitted from the light source 91 in the direction toward the display 11 are reflected and diffused, a case of using the grooves 95 is described as an example; however, the example is not limited thereto. There may be employed a configuration in which some light fluxes of the light fluxes that are emitted from the light source 91 in the direction toward the display 11 are reflected from the grooves 95 and diffused. In this case, for example, ink or the like is attached to the light guiding plate 92, and thereby a site, in which some light fluxes of the light fluxes that are emitted from the light source 91 in the direction toward the display 11 are reflected from and diffused, may be formed.

For example, the plurality of grooves 95 are not formed in a region through which the target light flux from the display 11 passes. For example, in the example, the plurality of grooves 95 are formed in a region corresponding to the region of the opening 97 and the opening 98. In other words, the plurality of grooves 95 are not formed in the region similar to the region of the opening 97 and the opening 98. The similar region does not need to be completely the same region but includes substantially the same region. It is needless to say that the region, in which the plurality of grooves 95 are not formed, is not limited to the region of the opening 97 and the opening 98. For example, there may be employed a configuration in which the plurality of grooves 95 are not formed in a region of the light guiding plate 92, through which the target light flux from the display 11 passes. As described above, for example, the plurality of grooves 95 are not formed in the region, through which the target light flux from the display 11 passes, and thereby it is possible to reduce the occurrence of the surface light emission by the surface light emitting unit 90 in the region through which the target light flux passes. In this manner, it is possible to reduce an overlap of surface light emission in the region of the target light flux by the surface light emitting unit 90, and thus it is possible to reduce an occurrence of difficulty in checking the target light flux.

In the example, the plurality of grooves 95 are not formed in the region, through which the target light flux from the display 11 passes, and thereby it is possible to reduce the occurrence of the surface light emission of the region through which the target light flux passes. However, the configuration in which the occurrence of the surface light emission is reduced in the region, through which the target light flux passes, is not limited thereto. For example, there may be employed a configuration in which the light guiding plate 92 is provided with an opening. For example, there may be employed a configuration in which the light guiding plate 92 is provided with an opening in the region through which the target light flux passes. In this case, the opening of the light guiding plate 92 may be formed in the region corresponding to the region of the opening 97 and the opening 98.

For example, the reflective sheet 93 is used to reflect the light flux emitted from the light sources 91, in the direction of the diffusion sheet 94. In addition, for example, the reflective sheet 93 reflects, in the direction of the diffusion sheet 94, the light flux diffused toward the reflective sheet 93 of the light flux diffused in the groove 95. For example, the reflective sheet 93 is made of a polyethylene terephthalate (PET) material. It is needless to say that the reflective sheet 93 is not limited to a sheet made of the PET material but may be a sheet made of a material that can reflect the light flux emitted from the light sources 91.

For example, the diffusion sheet 94 diffuses, in the direction to the flat mirror, the light flux emitted from the light sources 91. In addition, the diffusion sheet 94 diffuses, in the direction to the flat mirror, the light flux reflected from the reflective sheet and the groove. In this manner, the light flux is diffused from the diffusion sheet 94 toward the flat mirror 12, and thereby the surface light emission is performed from the periphery of the display 11.

The reflective sheet 93 and the diffusion sheet 94 are made of the PET material; however, the sheets have different reflectance from each other. For example, the reflectance of the reflective sheet 93 is higher than the reflectance of the diffusion sheet. For example, the reflective sheet 93 may be an opaque white sheet. In addition, for example, the diffusion sheet 94 may be a milk white sheet. It is needless to say that the reflective sheet 93 and the diffusion sheet 94 are not limited to the configuration described above. For example, the reflective sheet 93 may be configured to be capable of reflecting the light flux. In addition, for example, the diffusion sheet 94 may be configured to be capable of diffusing and emitting the light flux.

For example, the surface light emitting unit 90 emits light along with the display 11. For example, when the light source 91 turns on, in the surface light emitting unit 90, the light flux emitted from the light source 91 travels toward the display 11 via the light guiding plate 92. At this time, for example, a part of the light flux emitted from the light source 91 is reflected from the reflective sheet 93 toward the diffusion sheet 94. In addition, for example, a part of the light flux emitted from the light source 91 is reflected and diffused from the grooves 95 in the light guiding plate 92. A part of the light flux diffused from the grooves 95 travels toward the diffusion sheet 94. In addition, a part of the light flux diffused from the grooves 95 travels toward the reflective sheet 93, is reflected from the reflective sheet 93, and travels toward the diffusion sheet. For example, the light flux traveling toward the diffusion sheet 94 is diffused from the diffusion sheet 94 toward the flat mirror 12.

On the other hand, the target light flux from the display 11 passes through the opening 97 and is emitted toward the light guiding plate 92. The target light flux emitted to the light guiding plate 92 passes through the light guiding plate 92 and the opening 98 and is emitted to the flat mirror 12.

For example, in the example, the surface light emitting unit 90 causes the surface light emission to be performed on the periphery of the display 11 at a luminance value of 10% to 25% with respect to a luminance value of the display 11. In this manner, the periphery of the target presenting unit gets too bright, and thereby it is possible to reduce glare felt by the examinee during the subjective examination such that deterioration of measurement accuracy of the subjective examination is reduced. In addition, for example, the periphery of the target presenting unit gets too dark, and thereby an occurrence of a state in which it is not possible to suppress the reduction in retinal illuminance is reduced such that it is possible to perform the subjective measurement in a state in which the vision is close to the natural vision. It is needless to say that the example is not limited to the configuration in which the surface light emitting unit 90 causes the surface light emission to be performed on the periphery of the display 11 at the luminance value of 10% to 25% with respect to the luminance value of the display 11. The surface light emitting unit 90 may be configured to perform the surface light emission at a luminance value different from the luminance value of 10% to 25%. In this case, for example, the surface light emitting unit may be configured to cause the surface light emission to be performed on the periphery of the display 11 at a luminance value to the extent that it is possible to suppress the reduction in the retinal illuminance.

In the example, the surface light emitting unit 90 configured to cause the surface light emission to be performed on the periphery of the target presenting unit is described as an example; however, the example is not limited thereto. Any configuration may be used as long as it is possible to cause the surface light emission to be performed on the periphery of the target presenting unit. For example, there may be employed a configuration in which a reflective member is provided on the periphery of the target presenting unit, the reflective member is irradiated with a light flux from a light source provided at a separate position, the reflective member reflects the light flux, and surface light emission is performed from the periphery of the target presenting unit.

In the example, the configuration in which the surface light emitting unit 90 is disposed to surround the display the periphery thereof is described as an example; however, the example is not limited thereto. There may be also employed a configuration in which a surface light emitting unit is provided to the extent that it is possible to cause the surface light emission to be performed on the periphery of the target presenting unit. For example, there may be employed a configuration in which the surface light emitting unit is provided only in the rightward-leftward direction of the target presenting unit. In addition, for example, there may be employed a configuration in which the surface light emitting unit is provided only in the upward-downward direction of the target presenting unit.

<Controller>

Figure 12:
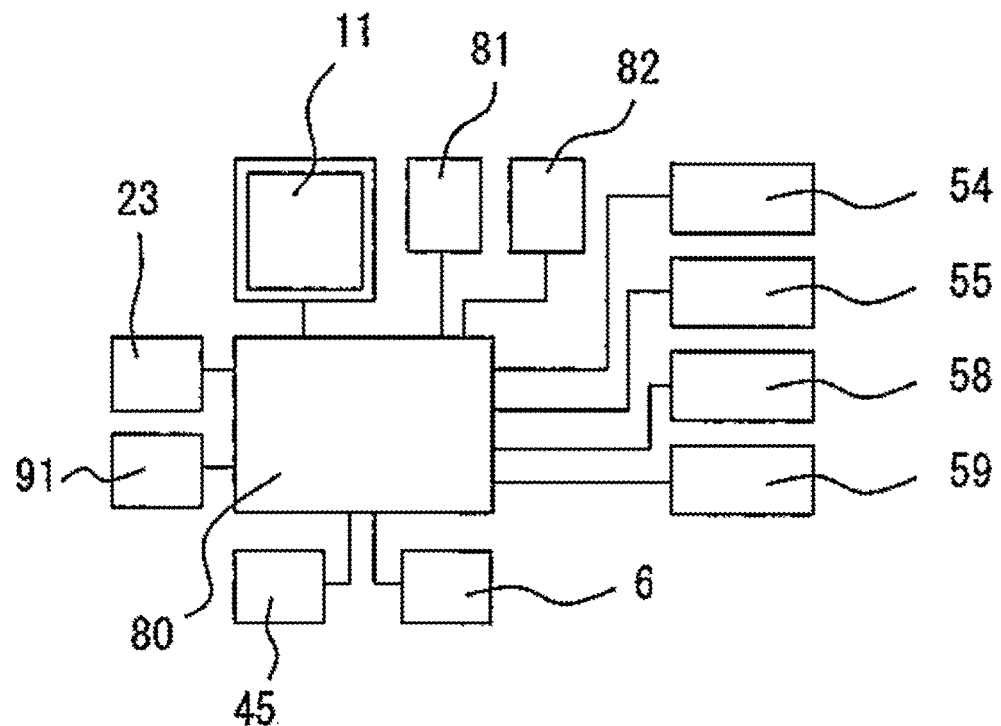
FIG. 12 is a diagram illustrating a schematic configuration of a control system in the subjective optometric apparatus.

For example, FIG. 12 is a diagram illustrating a schematic configuration of a control system in the subjective optometric apparatus 1.

For example, the display 11, the detector 45, a controller 81, a non-volatile memory 82, the light source 91, and the like are connected to the controller 80. In addition, for example, the motor 6 included in the drive unit 5 in the holding arm 4, the motor 23 included in the distance/near vision switching unit 20, the drive units (drives units 54, 55, 58, and 59) included in the members of the eye refractivity measuring unit 50, and the like are connected to the controller 80.

For example, the controller 80 includes a CPU (processor), a RAM, a ROM, and the like. For example, the CPU controls the members in the subjective optometric apparatus 1. For example, the RAM temporarily stores information. For example, in the ROM, various programs for controlling operations of the subjective optometric apparatus 1, examination target data, or the like is stored. The controller 80 may be configured to have a plurality of controllers (that is, a plurality of processors).

For example, the controller 81 is used to switch displays on the display 11 in the projection optical system 10, dispositions of the optical elements in the eye refractivity measuring unit 50. For example, a signal input from the controller 81 is input to the controller 80 via a cable not illustrated. In the example, there may be employed a configuration in which the signal from the controller 81 is input to the controller 80 via wireless communication of infrared or the like.

For example, the non-volatile memory 82 is a non-transitory storage medium that is capable of storing the storage content even when electric power supply is cut off. For example, as the non-volatile memory 82, it is possible to use a hard disk drive, a flash ROM, an OCT device, a USB memory, or the like. For example, in the non-volatile memory 82, many items of examination target data (for example, target data of visual acuity values of 0.1 to 2.0) of the Landolt ring target or the like are stored.

For example, in the example, the controller 80 performs switching between measurement modes of the subjective optometric apparatus 1, based on the detected results from the detector 45. For example, in the example, the controller 80 automatically performs switching between the measurement modes in response to the opening and closing of the cover 43. For example, when the detector 45 detects that the cover 43 is opened, the controller 80 sets the measurement mode to the second mode for checking the pupil position of the examinee. In addition, when the detector 45 detects that the cover 43 is closed, the controller 80 sets the measurement mode to the first mode for performing subjective examination on the examinee. In the example, a configuration in which the controller automatically performs switching between the measurement modes in response to the opening and closing of the cover 43 is provided; however, the example is not limited thereto. For example, the switching between the measurement modes may be manually performed by the examiner. In this case, there may be employed a case where the controller 81 to be described below is used to input a signal for switching between the measurement modes is input to the controller 80.

<Control Operation>

Control operations of the subjective optometric apparatus 1 having such a configuration are described. For example, the eye refractivity measuring unit 50 is positioned at the standby position before the start of the subjective examination. For example, as illustrated in FIG. 1, at the standby position in the example, the eye refractivity measuring unit 50 is in the lifted state. In addition, since the cover 43 is in a closed state, the measurement mode is set to the first mode for performing the subjective examination on the examinee.

For example, the examiner operates the controller 81 and lowers the eye refractivity measuring unit 50 to the measurement position illustrated in FIG. 13. For example, before the subjective examination is performed, the examiner measures an inter-pupil distance (PD) of the examinee in advance and inputs the measured PD into the subjective optometric apparatus 1. In this manner, the controller 80 drives the drive unit 58, adjusts the distance between the right and left lens chamber units 52, and changes the distance between the test windows 53 depending on the PD of the examinee's eye. For example, the controller 80 adjusts the distance between optical axes of the right and left test windows 53 in the horizontal direction (X direction) such that the distance becomes the same as the PD. In the example, when the words, the same, are used, meaning of substantially the same is included therein.

Subsequently, the examiner instructs the examinee to look into the test window 53. Here, for example, the examiner opens the cover 43 so as to check the inter-pupil distance PD of the examinee's eyes E. At this time, the detector 45 detects that the cover 43 is opened, and the controller 80 sets the measurement mode to the second mode for checking the pupil positions of the examinee.

Figure 14A:
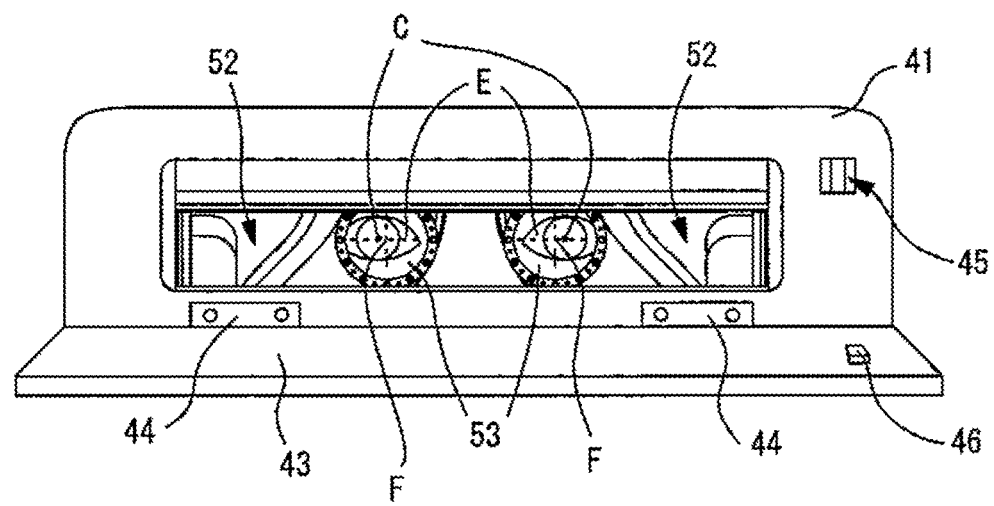
FIGS. 14A and 14B are views illustrating a state in which examinee's eyes are viewed via an observation window.
Figure 14B:
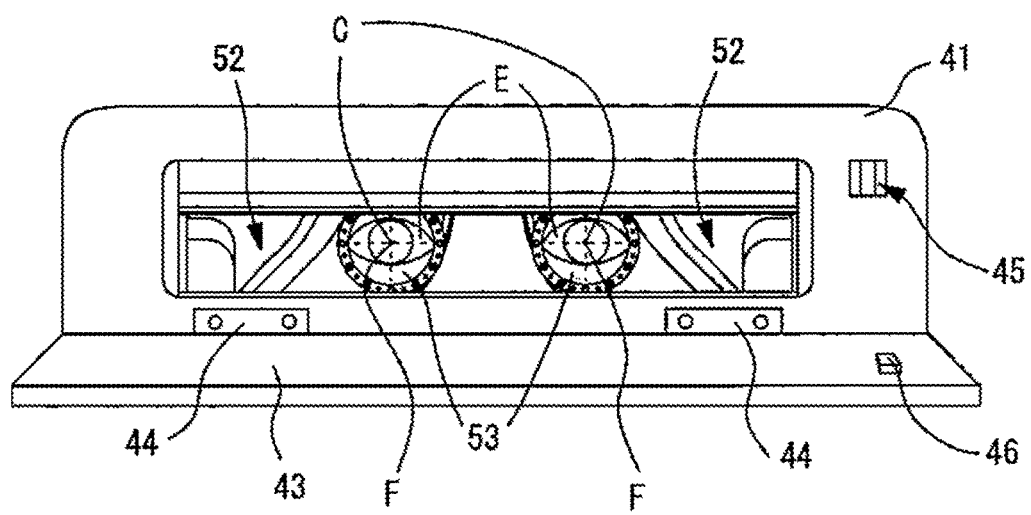

For example, FIG. 14 is a view illustrating a state in which examinee's eyes E are viewed via the observation window 41. FIG. 14(a) illustrates a state in which the position adjustment between the examinee's eye E and the test windows 53 is not appropriately performed. FIG. 14(b) illustrates a state in which the position adjustment between the examinee's eye E and the test windows 53 is appropriately performed. For example, the measurement mode is switched to the second mode, and thereby the controller 80 turns on lighting (not illustrated) for anterior eye part and illuminates the anterior eye part of the examinee's eye E.

In addition, for example, the controller 80 drives the drive unit 55, rotates the lens disc 57 included in the lens chamber unit 52, and disposes the lens for position adjustment, which is provided with the cross line, in the test window 53. For example, the examiner looks into the observation window 41 and checks the examinee's eye E via the inside of the housing 2 and the test window 53. For example, in the example, the lens for position adjustment is provided with the cross line such that the central position F of the cross line provided on the lens is coincident with the central position of the lens for position adjustment (that is, the central position of the test window 53).

For example, in a case where the examiner looks into the observation window 41, and the pupil centers C of the examinee's eyes E are not coincident with the central positions F of the cross lines (that is, the central positions of the lenses for position adjustment) as in FIG. 14(a), the examiner operates the controller 81 so as to adjust the distance between the right and left lens chamber units 52. In the example, the central position of the lens for position adjustment may mean a position of an optical axis of the lens for position adjustment. In other words, the central position of the test window 53 may be the position of the optical axis of the test window 53.

For example, when the examiner operates the controller 81 so as to adjust the distance between the right and left lens chamber units 52, the distance between the right and left lens chamber units 52 is adjusted such that the pupil positions C of the respective right and left examinee's eyes E are coincident with the central positions F of the cross lines provided on the lenses for position adjustment. For example, as illustrated in FIG. 14(b), in a case where the pupil positions C of the respective right and left examinee's eyes E are coincident with the central positions F of the cross lines provided on the lenses for position adjustment, the examiner determines that the position adjustment is appropriately performed.

Figure 15:
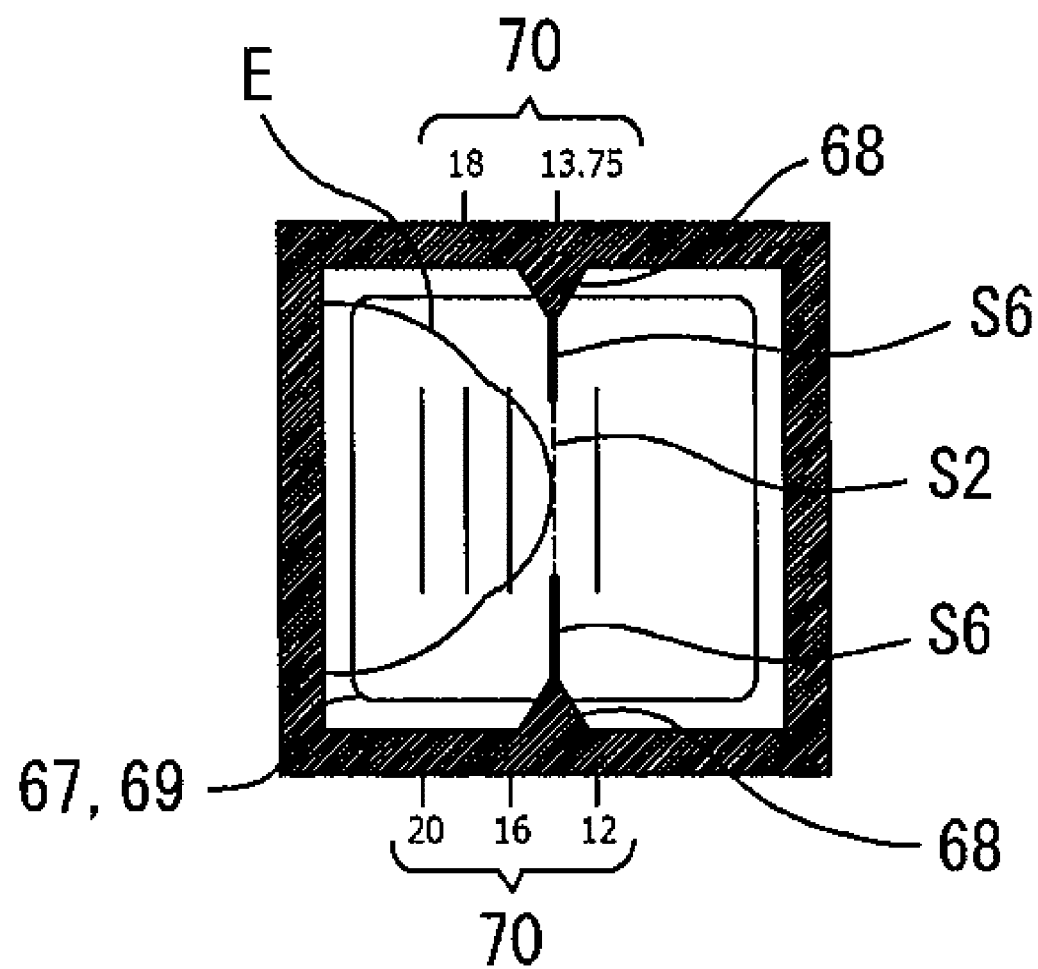
FIG. 15 is a view illustrating the aiming scale plate and the reticle plate during checking a cornea vertex position.

Subsequently, the examiner observes the checking window 65 via the light guiding unit 66 so as to check the inter-cornea vertex position of the examinee's eyes E. For example, FIG. 15 is a view illustrating the aiming scale plate 63 and the reticle plate 64 during the checking of the cornea vertex positions. The examiner searches for a position at which the first mark 67 on the aiming scale plate 63 and the second mark 69 on the reticle plate 64 match each other on the top, bottom, right, and left sides thereof and the first mark and the second mark overlap each other as one. Further, the examiner searches for a position at which the tip of the reticle 68 and the center line S6 match each other. For example, after performing such position adjustment, the examiner checks the side of the examinee's eye E. In addition, the examiner operates an adjustment knob with a forehead rest not illustrated and adjusts the position of the forehead rest 51 in the eye refractivity measuring unit 50. In this manner, the cornea vertexes of the examinee's eyes E are caused to move and can be coincident with a scale line S2.

For example, when the position adjustment of the examinee's eyes E with respect to the eye refractivity measuring unit 50 is ended, the examiner closes the cover 43 and starts the subjective examination. At this time, the detector 45 detects that the cover 43 is closed, and the controller 80 switches the measurement mode to the first mode for performing the subjective examination on the examinee.

For example, in a case of performing the distance vision examination (refer to FIG. 4(a)), the controller 80 turns on the display 11. For example, the target light flux is emitted toward the flat mirror 12 from the display 11 held by the holder 21. The target light flux is reflected from the flat mirror 12 and the concave mirror 13 and is guided to the examinee's eye E via the flat mirror 12 again. In addition, for example, in a case of performing the near vision examination (refer to FIG. 4(b)), the display 11 moves along with the holder 21 and is disposed at a short distance (for example, a distance apart by 40 cm) with respect to the examinee's eye E. The target light flux is emitted toward the flat mirror 12 from the display 11. The target light flux is reflected from the flat mirror 12 and is guided to the examinee's eye E.

On the other hand, the display 11 turns on, and at the same time the controller 80 turns on the surface light emitting unit 90 disposed around the display 11. For example, the light flux emitted from the surface light emitting unit 90 is reflected from both of the flat mirror 12 and the concave mirror 13 and is guided to the examinee's eye E via the flat mirror 12 again.

For example, during the distance vision examination and the near vision examination, the examiner operates the controller 81 so as to display the examination target on the screen of the display 11. The controller 80 reads corresponding examination target data from the non-volatile memory 82 in response to an input signal from the controller 81 and controls the display of the display 11. The examination target displayed on the display 11 is presented to the examinee's eye E via the test window 53 and the presentation window 3 in the eye refractivity measuring unit 50. In addition, for example, the surface light emitting unit 90 causes the surface light emission to be performed on the periphery of the display 11. For example, after the examiner switches examination target, the examiner asks the examiner about the appearance of the examination target. For example, in a case where the examinee's answer is correct, the target is switched to a target corresponding to a one-level-high visual acuity value. In addition, for example, in a case where the examinee's answer is incorrect, the target is switched to a target corresponding to a one-level-low visual acuity value. By performing a visual function test, the examiner can acquire optical properties of the examinee's eye E (for example, a spherical diopter power S, a cylindrical power C, an astigmatic axis angle A, or the like).

For example, when the distance vision examination or the near vision examination is ended, the examiner performs a temporary frame test on the examinee's eye E. At this time, the examiner operates the controller 81 and lifts the eye refractivity measuring unit to the standby position illustrated in FIG. 1. In addition, the examiner enables the examinee to wear a temporary frame (a trial frame or a test frame) and checks a wearing feeling while switching between lenses (trial lenses) having various powers.

As described above, for example, in the example, the subjective optometric apparatus includes the observation unit for observing, via the presentation window, the positional relationship between the examinee's eye and the eye refractivity measuring unit that changes the optical property of the target light flux output from the inside of the housing to the outside of the housing. In this manner, the examiner can easily check the positional relationship between the eye refractivity measuring unit and the examinee's eye and can easily perform position adjustment between the examinee's eye and the eye refractivity measuring unit.

In addition, for example, in the embodiment, the observation unit is disposed outside of the optical path through which the target light flux passes. Therefore, the observation unit does not block the optical path through which the target light flux passes, and thus it is possible to reduce an occurrence of a defect in the examination target. Hence, it is possible to present an examination target suitable for the examinee's eye.

In addition, for example, in the example, the observation unit includes the observation window for observing the positional relationship between the eye refractivity measuring unit and the examinee's eye. Therefore, the examiner directly looks into the observation window, thereby making it possible to check the pupil position of the examinee's eye and the position of the eye refractivity measuring unit. The examiner can easily check the pupil position of the examinee's eye and the position of the eye refractivity measuring unit in a simple configuration.

In addition, for example, in the example, the observation unit includes the shielding portion for shielding the target light flux. Therefore, the target light flux from the target presenting unit is not guided to the examiner, and thus it is possible to observe the examinee's eye from the observation window without feeling dazzling. Hence, when the examinee checks the target and performs the examination, it is possible to reduce an occurrence of reflection of the target on the observation window and interference with the examination.

In addition, for example, in the example, the observation unit includes the cover that is openable and closeable with respect to the observation window and the detecting means that detects opening and closing of the cover. In addition, for example, the subjective optometric apparatus includes the controlling means that performs switching between the first mode for performing subjective examination on the examinee and the second mode for checking the pupil position of the examinee, based on the detected results from the detecting means. In this manner, setting for checking the pupil position of the examinee's eye and the position of the eye refractivity measuring unit is manually performed, and thus the examiner can smoothly prepare the subjective examination.

In addition, for example, in this example, the subjective optometric apparatus includes: the cornea position alignment optical system that is disposed in the eye refractivity measuring unit and is used to check the inter-vertex distance between the lens wearing reference position and the cornea vertex of the examinee's eye; the checking window for checking the cornea position alignment optical system disposed in the inside of the eye refractivity measuring unit from the outside of the eye refractivity measuring unit; and the light guiding unit for observing the checking window. In this manner, the examiner can easily check the positional relationship between the eye refractivity measuring unit and the position of the cornea vertex of the examinee's eye and can easily perform the position adjustment between the examinee's eye and the eye refractivity measuring unit.

In addition, for example, in the example, in the subjective optometric apparatus, the housing and the eye refractivity measuring unit are disposed to be close to each other, and thereby it is possible to perform connection in a space saving manner in the subjective optometric apparatus. In addition, particularly, in a case of the subjective optometric apparatus in which the housing and the eye refractivity measuring unit are disposed to be close to each other, a distance from the housing to the eye refractivity measuring unit is shortened. Therefore, it is difficult to check the positional relationship between the position of the eye refractivity measuring unit through a space between the housing and the eye refractivity measuring unit and the pupil positions or the cornea vertex positions of the examinee's eyes. Therefore, in the case of the subjective optometric apparatus in which the housing and the eye refractivity measuring unit are disposed to be close to each other, the technology of this disclosure is particularly effective because it is possible to easily check the positional relationship between the eye refractivity measuring unit and the examinee's eye.

For example, in the example, the subjective optometric apparatus includes: the projection optical system that has the target presenting unit which emits the target light flux and that projects, onto the examinee's eye, the target light flux emitted from the target presenting unit; the housing that accommodates the projection optical system; and the light emitting means that is the member different from the target presenting unit and causes surface light emission to be performed on the periphery of the target presenting unit. According to such a configuration, it is possible to suppress reduction in retinal illuminance, and it is possible to perform the subjective measurement in a state in which a vision close to a natural vision is obtained.

For example, in the example, in the subjective optometric apparatus, the housing and the eye refractivity measuring unit are disposed to be close to each other, and thereby it is possible to perform connection in a space saving manner in the subjective optometric apparatus. In addition, particularly, in the case of the subjective optometric apparatus in which the housing and the eye refractivity measuring unit are disposed to be close to each other, the distance from the housing to the eye refractivity measuring unit is shortened, and thus the retinal illuminance becomes low. Therefore, in the case of the subjective optometric apparatus in which the housing and the eye refractivity measuring unit are disposed to be close to each other, the technology of this disclosure is particularly effective because it is possible to an occurrence of the low retinal illuminance.

For example, in the example, the subjective optometric apparatus has the configuration in which the light emitting means surrounds the target presenting unit the periphery thereof. In this manner, the light emitting means is disposed to surround the target presenting unit the periphery thereof, and thus it is possible to reduce uneven illumination on the periphery of the target presenting unit. In other words, it is possible to evenly illuminate the periphery of the target presenting unit.

<Modification Example>

In the example, the configuration in which the optical axis L3 and the optical axis L4 of the projection optical system 10 are coaxial to each other during the distance vision examination and the near vision examination; however, the configuration is not limited thereto. For example, in the example, the target light flux may be possible to be guided to the examinee's eye E, or a configuration in which the target light fluxes pass through separate optical paths from each other during the distance vision examination and the near vision examination may be employed.

In the example, the configuration in which the flat mirror 12 included in the projection optical system 10 is disposed in a fixed manner is described as an example; however, the example is not limited thereto. For example, the flat mirror 12 may be capable of adjusting the rotating angle.

In this case, the flat mirror 12 is a drive unit for performing driving and is configured to include a rotary shaft and a drive unit. For example, the rotary shaft is connected to the flat mirror. In addition, the drive unit rotates the flat mirror around a horizontal axis, and thereby the rotating angle is adjusted. In this manner, it is possible to change the optical path of the target light flux that is reflected from the concave mirror and is incident to the flat mirror. In other words, the flat mirror is rotated, and thereby it is possible to change the optical axis L4 such that the target light flux is presented to the examinee's eye E. Therefore, even in a case where a height of the examinee's eye E is different for each examinee, it is possible to guide the target light flux to the examinee's eye E. Such a drive unit may be configured to rotate the flat mirror in the frontward-rearward direction or the upward-downward direction with respect to the examinee.

In the example, the configuration in which the observation window 41 is disposed at the position at which it is possible to view the examinee's eye E from the examiner's eye OE is described as an example; however, the example is not limited thereto. For example, the observation window 41 may be disposed at a position at which it is not possible to directly check the pupil position C of the examinee's eye E from the examiner's eye OE (for example, on the top surface or the side surface of the housing 2). In this case, for example, another mirror or the like may be disposed inside the housing 2, and thereby it may be possible to check the pupil position C of the examinee's eye E via the mirror.

In the example, the configuration in which the observation window 41 is disposed outside of the optical path of the target light flux is described; however, the example is not limited thereto. For example, the observation window 41 may be disposed outside of the optical path by being disposed above the optical path of the target light flux. In this case, for example, there is provided a configuration in which the observation window 41 is provided below the flat mirror 12 is provided. In addition, for example, by using the beam splitter instead of the flat mirror 12, the observation window 41 can be disposed outside of the optical path of the target light flux. For example, the beam splitter reflects a part of the target light flux incident to the beam splitter and transmits a part thereof. Therefore, the target light flux is guided to the examinee's eye E, and it is possible to present correct target. In addition, the observation window 41 is disposed in a transmitting direction of the beam splitter, and thereby the target light flux is also guided to the examiner's eye OE. Therefore, it is possible to check the positional relationship between the eye refractivity measuring unit 50 and the examinee's eye E.

In the example, the configuration in which the observation window 41 is provided as the observation unit 40 is described; however, the example is not limited thereto. For example, there may be employed a configuration in which the imaging optical system is provided as the observation unit. In this case, for example, the observation unit may be configured to include the imaging optical system provided with the imaging element that images the eye refractivity measuring unit and the examinee's eye via the presentation window. For example, the imaging element provided in the imaging optical system images the eye refractivity measuring unit 50 and the examinee's eye E via the presentation window 3. For example, an image of the imaged examinee's eye may be displayed on a monitor of the controller 81 through wireless communication or the like. In addition, for example, the image of the imaged examinee's eye may be configured to be printed. In this case, for example, there is provided a configuration in which the image is output and transmitted to a printer or the like via a communication cable or the like. Even in the configuration, the examiner checks the image of the examinee's eye E acquired by the imaging optical system, and thereby it is possible to determine the positional relationship between the eye refractivity measuring unit 50 and the examinee's eye E. According to the configuration, for example, the examiner can easily check the pupil position of the examinee's eye and the position of the eye refractivity measuring unit in a simple configuration. For example, the imaging optical system may be disposed at a position at which it is possible to image the examinee's eye E. For example, as described above, in a case of using the beam splitter instead of the flat mirror 12, the imaging optical system may be disposed in the transmitting direction of the beam splitter.

In the example, there is no need to provide the observation window 41. For example, as a configuration without the observation window 41, there is provided a configuration in which it is possible to detach the flat mirror 12. In this case, for example, the flat mirror 12 is provided on the back surface of the housing 2 and the back surface of the housing 2 is detached. In this manner, it may be possible to detach the flat mirror 12. According to this configuration, even when the observation window 41 is not provided, the examiner can detach the back surface of the housing 2 and check the positional relationship between the eye refractivity measuring unit 50 and the examinee's eye E. When the detached back surface of the housing 2 is returned back, it is possible to present the examination target to the examinee's eye E by the projection optical system 10.

Figure 16A:
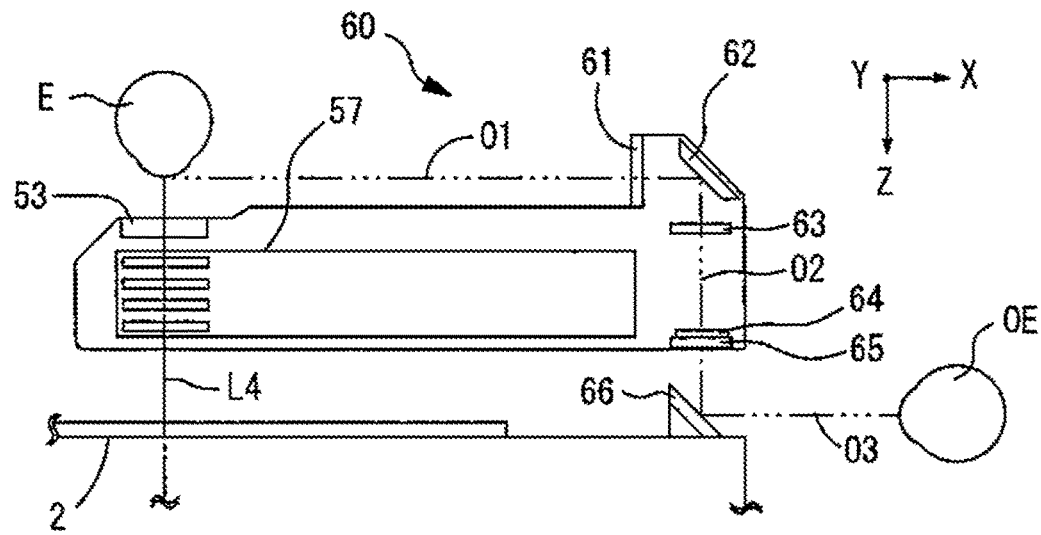
FIGS. 16A and 16B are views illustrating a modification example of a light guiding unit.
Figure 16B:
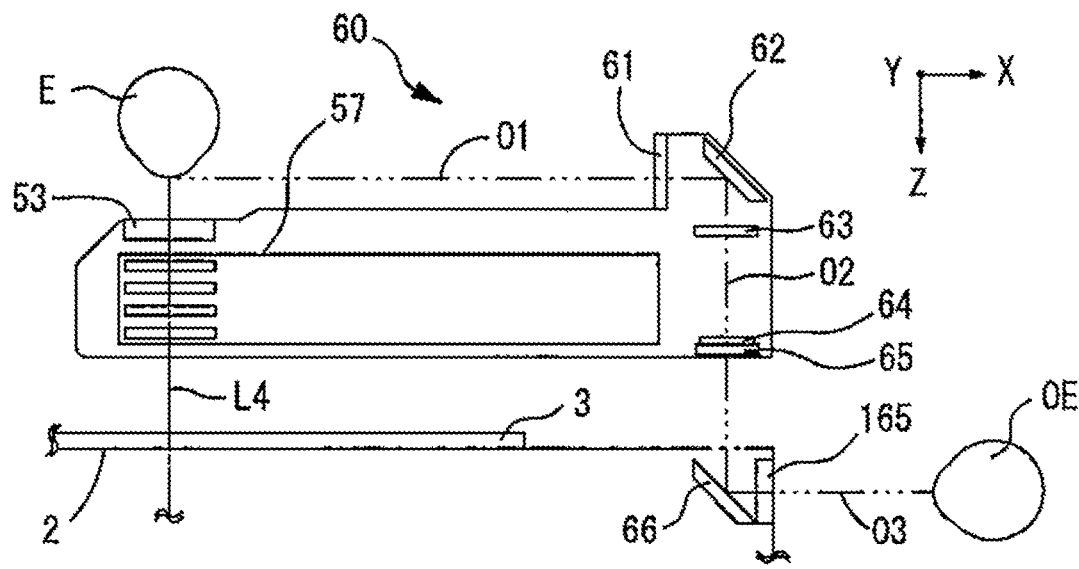

In the example, the configuration in which the light guiding unit 66 provided in the cornea position alignment optical system 60 is provided in the eye refractivity measuring unit 50 is described, the example is not limited thereto. FIG. 16 is a view illustrating a modification example of the light guiding unit 66. For example, as illustrated in FIG. 16(a), the light guiding unit 66 may be provided outside the housing 2. In this case, the observation light of the examinee's eye E reflected by the light guiding unit 66 is projected on the examiner's eye OE. In addition, for example, as illustrated in FIG. 16(b), the light guiding unit 66 may be provided inside the housing 2. In this case, a checking window 165 may be provided on the side surface of the housing 2. In this manner, the observation light of the examinee's eye E is reflected from the light guiding unit 66 and is projected on the examiner's eye OE through the checking window 165. For example, in the example, such a configuration is provided, and thereby it is possible to observe the side of the examinee's eye E, and it is possible to check the reference position or the inter-cornea vertex distance VD during the lens wearing on the examinee's eye E.

In addition, in the example, the configuration in which a mirror is used as the light guiding unit 66 is described as an example; however, the example is not limited thereto. The light guiding unit 66 may be configured to be capable of observing the checking window 65. In other words, the imaging optical system for imaging the checking window 65 may be provided. In this case, the examiner can check the reference position or the inter-cornea vertex distance VD during the lens wearing by using the image of the examinee's eye E imaged by the imaging optical system.

In the example, the first mark 67 of the aiming scale plate 63 and the second mark 69 of the reticle plate 64 have the rectangular shape; however, the shape thereof is not limited thereto. The first mark 67 and the second mark 69 may have a single line shape. In addition, if the first mark 67 and the second mark 69 are in different colors from each other, it is possible to further improve the visibility.

In addition, for example, for a person who has the sharp face line, a person who has a deep eye, or the like, it is difficult to move the examinee's eye E to the scale line S2 of the aiming scale plate 63 in some cases. At this time, the cornea vertexes of the examinee's eyes E may be checked by using any one scale line of the other scale lines S1 and S3 to S5. For example, there may be employed a configuration in which the controller 80 obtains the refractivity at the reference position from a predetermined conversion expression, based on VD of the used scale line.

In the example, the configuration in which the surface light emitting unit 90 turns on along with turning on of the display 11 is described as an example; however, the example is not limited thereto. For example, the surface light emitting unit 90 may turn on at a timing different from a timing when the display 11 turns on.

For example, the surface light emitting unit 90 may perform control such that it is possible to turn on and off at an arbitrary cycle. Such a configuration is provided, and thereby the surface light emitting unit 90 may serve as a light source for a flicker test.

In the example, there may be employed a configuration in which it is possible to set whether or not to turn on the surface light emitting unit 90. For example, in a case where a lighting switch of the surface light emitting unit 90 is selected by the examiner, the surface light emitting unit 90 may turn on by the examiner. In addition, for example, environmental light such as ambient light is detected, and thereby the surface light emitting unit 90 may turn on based on the detected results of the environmental light.

Control of the luminance value obtained when the surface light emitting unit 90 turns on may be performed such that it is possible to emit light with high luminance. For example, such control is performed, and thereby the surface light emitting unit 90 may serve as a light source of glare light.

It may be possible to change the luminance value of the surface light emitting unit 90 into an arbitrary luminance value. For example, there may be employed a configuration in which the examiner changes the luminance value into an arbitrary value by using a luminance value changing switch. In addition, for example, there may be employed a configuration in which environmental light is detected, and thereby the luminance value is changed based on the detected results of the environmental light such as ambient light. In addition, for example, a luminance value may be set in advance to vary depending on the target displayed on the target presenting unit. In this case, the luminance value of the surface light emitting unit 90 may be changed based on a change in the target.

What is claimed is:

1. A subjective optometric apparatus comprising:
   a projection optical system that includes a target presenting unit configured to emit a target light flux, the projection optical system being configured to project, onto an examinee's eye, the target light flux emitted from the target presenting unit;
   a housing configured to accommodate the projection optical system;
   a presentation window configured to project the target light flux onto the examinee's eye by transmitting the target light flux emitted from the projection optical system and outputting the target light flux from an inside of the housing to an outside of the housing;
   an eye refractivity measuring unit configured to change an optical property of the target light flux output from the inside of the housing to outside of the housing and
   an observation unit configured to permit observation by an examiner from an observation window or by an imaging device, via the presentation window, a positional relationship between the examinee's eye and the eye refractivity measuring unit; and
   wherein the eye refractivity measuring unit is disposed outside of the housing facing the presentation window.

2. The subjective optometric apparatus according to claim 1, wherein the observation unit is disposed outside of an optical path through which the target light flux passes.

3. The subjective optometric apparatus according to claim 1,
   wherein the observation unit further includes a shielding portion configured to shield the target light flux emitted from the projection optical system.

4. The subjective optometric apparatus according to claim 1,
   wherein the observation unit further includes:
      a cover that is openable and closeable with respect to the observation window; and
      a detector configured to detect opening and closing of the cover, and
   wherein the subjective optometric apparatus includes a controller configured to perform switching between a first mode for performing subjective examination on an examinee and a second mode for checking a pupil position of the examinee, based on detected results from the detector.

5. The subjective optometric apparatus according to claim 3,
   wherein the observation unit further includes:
      a cover that is openable and closeable with respect to the observation window; and
      a detector configured to detect opening and closing of the cover, and
   wherein the subjective optometric apparatus includes a controller configured to perform switching between a first mode for performing subjective examination on an examinee and a second mode for checking a pupil position of the examinee, based on detected results from the detector.

6. The subjective optometric apparatus according to claim 1,
   wherein the observation unit includes an imaging optical system provided with an imaging element configured to image the eye refractivity measuring unit and the examinee's eye via the presentation window.

7. The subjective optometric apparatus according to claim 1, further comprising the eye refractivity measuring unit,
   wherein the target light flux is projected onto the examinee's eye via the eye refractivity measuring unit.

8. The subjective optometric apparatus according to claim 1, further comprising:
   a cornea position alignment optical system that is disposed in the eye refractivity measuring unit and is used to check an inter-vertex distance between a lens wearing reference position and a cornea vertex of the examinee's eye;

a checking window for checking the cornea position alignment optical system from the outside of the eye refractivity measuring unit; and a light guiding unit configured to observe the checking window.

9. The subjective optometric apparatus according to claim 1, wherein the observation window is disposed on a side of the housing opposite to a side of the housing on which the presentation window is disposed.

10. The subjective optometric apparatus according to claim 1, wherein the observation unit is configured to permit the examiner to observe the positional relationship between the examinee's eye and the refractivity measuring unit when viewing the observation window from outside a space between the presentation window and the refractivity measuring unit.

11. The subjective optometric apparatus according to claim 1, wherein, when observing the positional relationship between the examinee's eye and the eye refractivity measuring unit, the distance between the eye refractivity measuring unit and the presentation window is 1 meter or less.

12. The subjective optometric apparatus according to claim 11, wherein the distance is about 500 mm or 135 mm or 70 mm.

13. A subjective optometric apparatus comprising:

a projection optical system that has a target presenting unit configured to emit a target light flux and configured to project, onto an examinee's eye, the target light flux emitted from the target presenting unit;

a housing that accommodates the projection optical system;

a presentation window configured to project the target light flux onto the examinee's eye by transmitting the target light flux emitted from the projection optical system and outputting the target light flux from an inside of the housing to an outside of the housing;

an eye refractivity measuring unit configured to change an optical property of the target light flux output from the inside of the housing to the outside of the housing and that includes a pair of right and left lens chamber units that dispose optical elements in a test window in a switchable manner;

a cornea position alignment optical system that is disposed in the eye refractivity measuring unit and is used to check an inter-vertex distance between a lens wearing reference position and a cornea vertex of the examinee's eye;

a checking window for checking the cornea position alignment optical system disposed outside of the eye refractivity measuring unit; and a light guiding unit configured to observe the checking window; and wherein the eye refractivity measuring unit is disposed outside of the housing facing the presentation window and the housing comprises an observation window or an imaging device that permits observation by an examiner of a positional relationship between the examinee's eye and the eye refractivity measuring unit.

14. The subjective optometric apparatus according to claim 7, wherein the housing and the eye refractivity measuring unit are disposed to be close to each other.

15. The subjective optometric apparatus according to claim 8, wherein the housing and the eye refractivity measuring unit are disposed to be close to each other.

16. The subjective optometric apparatus according to claim 13, wherein the housing and the eye refractivity measuring unit are disposed to be close to each other.

* * * * *